United States Patent [19]

Condon et al.

[11] Patent Number: 5,484,762
[45] Date of Patent: Jan. 16, 1996

[54] ARYLOXY-N-(SUBSTITUTED PHENYL) BENZOTRIAZOLE HERBICIDAL AGENTS

[75] Inventors: Michael E. Condon, Lawrenceville; Alvin D. Crews, Jr., Voorhees; Mark C. Manfredi, Hamilton, all of N.J.

[73] Assignee: American Cyanamid Company, Wayne, N.J.

[21] Appl. No.: 386,975

[22] Filed: Feb. 10, 1995

[51] Int. Cl.$^6$ .................. A01N 43/647; C07D 401/12; C07D 249/20
[52] U.S. Cl. .................. 504/261; 504/253; 546/271; 548/259
[58] Field of Search .................. 546/271; 548/259; 504/253, 261

[56] References Cited

U.S. PATENT DOCUMENTS 5,324,711  6/1994  Nielsen et al. .................. 548/259

Primary Examiner—Patricia L. Morris
Attorney, Agent, or Firm—Peggy A. Climenson

[57] ABSTRACT

There is provided an aryloxy-N-(substituted phenyl)benzotriazole compound having the structural formula I

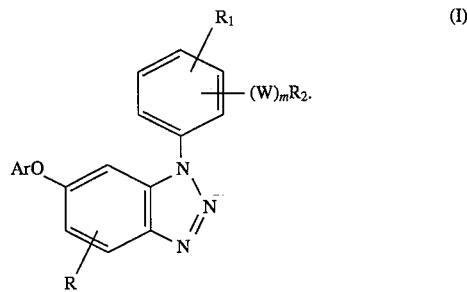

Further provided are a composition and a method comprising that compound for the control of undesirable plant species.

19 Claims, No Drawings

ARYLOXY-N-(SUBSTITUTED PHENYL) BENZOTRIAZOLE HERBICIDAL AGENTS

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

Certain aryloxybenzotriazole compounds are known to have herbicidal or fungicidal activity (U.S. Pat. No. 4,911,754; EP 108908-A2; EP 178708-A2; and EP 355049-A2). And certain N-phenylbenzotriazole compounds are known to have herbicidal activity (U.S. Pat. No. 4,240,822 and EP 107216-A1). However, benzotriazole compounds substituted with an aryloxy group and a N-phenyl group are not described in the art.

It is therefore an object of the present invention to provide compounds which are highly effective for controlling undesirable plant species.

It is also an object of the present invention to provide a method for controlling undesirable plant species.

These and other objects of the present invention will become more apparent from the detailed description thereof set forth below.

SUMMARY OF THE INVENTION

The present invention describes aryloxy-N-(substituted phenyl) benzotriazole compounds which are useful as herbicidal agents.

The aryloxy-N-(substituted phenyl)benzotriazole compounds of the present invention have the structural formula I

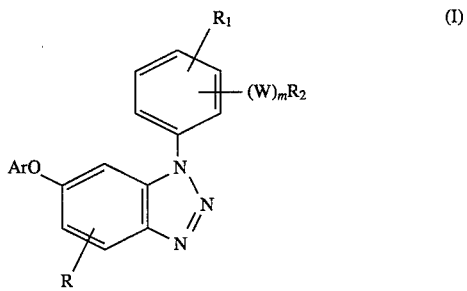

wherein
Ar is

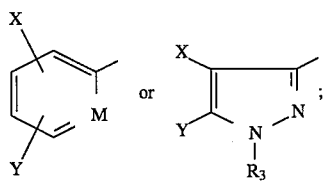

M is N or CZ;

X, Y and Z are each independently hydrogen, halogen, $C_1$–$C_4$alkyl, $C_1$–$C_4$haloalkyl, $C_1$–$C_4$alkoxy, $C_1$–$C_4$haloalkoxy, cyano, nitro or $S(O)_p R_4$ with the proviso that X, Y and Z cannot simultaneously be nitro;

R is hydrogen, halogen, nitro, cyano, $C_1$–$C_4$alkyl, $C_1$–$C_4$haloalkyl, $C_1$–$C_4$alkoxy, $C_1$–$C_4$haloalkoxy or $S(O)_q R_5$;

p and q are each independently on integer of 0, 1 or 2;

$R_4$ and $R_5$ are each independently $C_1$–$C_4$alkyl optionally substituted with one or more halogen atoms;

$R_3$ is $C_1$–$C_4$alkyl;

$R_1$ is hydrogen, halogen, $C_1$–$C_4$alkyl or $C_1$–$C_4$haloalkyl;

W is O, S or $NR_6$;

$R_6$ is hydrogen or $C_1$–$C_4$alkyl;

m is an integer of 0 or 1;

$R_2$ is V or $R_7V$;

$R_7$ is $C_1$–$C_5$alkylene optionally substituted with one or more halogen, $C_1$–$C_4$alkyl, $C_1$–$C_4$haloalkyl or $C_3$–$C_6$cycloalkyl groups;

V is cyano, $C(O)R_8$, $C(Q)R_9$, $CH_2OC(O)R_{10}$, $CH_2OR_9$, $CH(OR_{11})_2$, $N(R_9)SO_2R_{12}$ or $C_2$–$C_6$alkenyl substituted with one $CO_2R_{10}$ group;

$R_8$ is OH, $OR_{13}$, $NR_{14}R_{15}$ or $N(R_9)SO_2R_{12}$;

Q is O, $NOC(R_{16}R_{17})CO_2R_{11}$ or $NOR_{10}$;

$R_9$ is hydrogen or $C_1$–$C_4$alkyl optionally substituted with $C_1$–$C_4$alkoxy;

$R_{10}$ is hydrogen, $C_1$–$C_4$alkyl, benzyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{11}$ is $C_1$–$C_4$alkyl, —$(CH_2)_3$— or —$(CH_2)_4$—;

$R_{12}$ is $C_1$–$C_4$alkyl, $C_1$–$C_4$haloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{13}$ is
  $C_1$–$C_6$alkyl optionally substituted with $C_1$–$C_4$ alkoxy, $C_1$–$C_4$alkylthio, halogen, hydroxy, $C_3$–$C_6$cycloalkyl, furyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups,
  $C_3$–$C_6$alkenyl optionally substituted with $C_1$–$C_4$alkoxy, halogen, $C_3$–$C_6$cycloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups,
  $C_3$–$C_6$alkynyl optionally substituted with $C_1$–$C_4$alkoxy or halogen,
  $C_3$–$C_6$cycloalkyl,
  $N=C(R_{16}R_{17})$,
  $C(R_{16}R_{17})CO_2R_9$ or
  an alkali metal, alkaline earth metal, manganese, copper, zinc, cobalt, silver, nickel, ammonium or organic ammonium cation;

$R_{14}$ and $R_{15}$ are each independently hydrogen, $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups; and $R_{16}$ and $R_{17}$ are each independently hydrogen or $C_1$–$C_4$alkyl.

This invention also relates to compositions containing those compounds and methods for using those compounds and compositions. Advantageously, it has been found that the compounds of the present invention, and compositions containing them, are useful for the control of undesirable plant species. The compounds of the present invention are especially useful for the post-emergence control of undesirable plant species.

DETAILED DESCRIPTION OF THE INVENTION

The present invention provides a method for controlling undesirable plant species which comprises applying to the foliage of said plants or to the soil or water containing seeds or other propagating organs thereof, a herbicidally effective amount of a formula I, aryloxy-N-(substituted phenyl)benzotriazole compound.

The aryloxy-N-(substituted phenyl)benzotriazole compounds of the present invention have the structural formula I

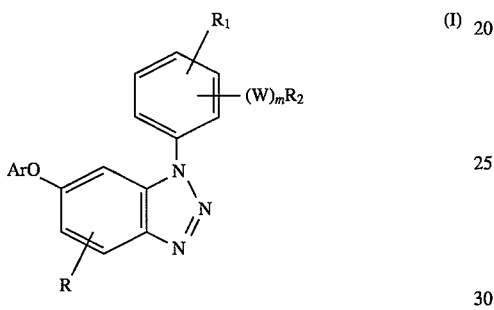

wherein
Ar is

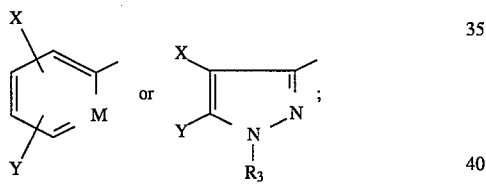

M is N or CZ;

X, Y and Z are each independently hydrogen, halogen, $C_1$–$C_4$alkyl, $C_1$–$C_4$haloalkyl, $C_1$–$C_4$alkoxy, $C_1$–$C_4$haloalkoxy, cyano, nitro or $S(O)_pR_4$ with the proviso that X, Y and Z cannot simultaneously be nitro;

R is hydrogen, halogen, nitro, cyano, $C_1$–$C_4$alkyl, $C_1$–$C_4$haloalkyl, $C_1$–$C_4$alkoxy, $C_1$–$C_4$haloalkoxy or $S(O)_qR_5$;

p and q are each independently an integer of 0, 1 or 2;

$R_4$ and $R_5$ are each independently $C_1$–$C_4$alkyl optionally substituted with one or more halogen atoms;

$R_3$ is $C_1$–$C_4$alkyl;

$R_1$ is hydrogen, halogen, $C_1$–$C_4$alkyl or $C_1$–$C_4$haloalkyl;

W is O, S or $NR_6$;

$R_6$ is hydrogen or $C_1$–$C_4$alkyl;

m is an integer of 0 or 1;

$R_2$ is V or $R_7V$;

$R_7$ is $C_1$–$C_5$alkylene optionally substituted with one or more halogen, $C_1$–$C_4$alkyl, $C_1$–$C_4$haloalkyl or $C_3$–$C_6$cycloalkyl groups;

V is cyano, $C(O)R_8$, $C(Q)R_9$, $CH_2OC(O)R_{10}$, $CH_2OR_9$, $CH(OR_{11})_2$, $N(R_9)SO_2R_{12}$ or $C_2$–$C_6$alkenyl substituted with one $CO_2R_{10}$ group;

$R_8$ is OH, $OR_{13}$, $NR_{14}R_{15}$ or $N(R_9)SO_2R_{12}$;

Q is O, $NOC(R_{16}R_{17})CO_2R_{11}$ or $NOR_{10}$;

$R_9$ is hydrogen or $C_1$–$C_4$alkyl optionally substituted with $C_1$–$C_4$alkoxy;

$R_{10}$ is hydrogen, $C_1$–$C_4$alkyl, benzyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{11}$ is $C_1$–$C_4$alkyl, —$(CH_2)_3$— or —$(CH_2)_4$—;

$R_{12}$ is $C_1$–$C_4$alkyl, $C_1$–$C_4$haloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{13}$ is $C_1$–$C_6$alkyl optionally substituted with $C_1$–$C_4$alkoxy, $C_1$–$C_4$alkylthio, halogen, hydroxy, $C_3$–$C_6$cycloalkyl, furyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, $C_3$–$C_6$alkenyl optionally substituted with $C_1$–$C_4$alkoxy, halogen, $C_3$–$C_6$cycloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, $C_3$–$C_6$alkynyl optionally substituted with $C_1$–$C_4$alkoxy or halogen, $C_3$–$C_6$cycloalkyl, $N=C(R_{16}R_{17})$, $C(R_{16}R_{17})CO_2R_9$ or an alkali metal, alkaline earth metal, manganese, copper, zinc, cobalt, silver, nickel, ammonium or organic ammonium cation;

$R_{14}$ and $R_{15}$ are each independently hydrogen, $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups; and $R_{16}$ and $R_{17}$ are each independently hydrogen or $C_1$–$C_4$alkyl.

Preferred formula I compounds of the present invention are those wherein

Ar is

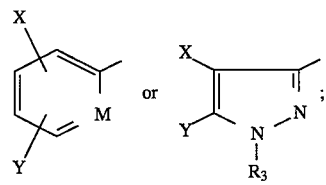

M is N or CZ;

X, Y and Z are each independently hydrogen, halogen or $C_1$–$C_4$haloalkyl;

$R_3$ is $C_1$–$C_4$alkyl;

R is hydrogen or halogen;

$R_1$ is hydrogen;

W is O;

m is an integer of 0 or 1;

$R_2$ is V or $R_7V$;

$R_7$ is $C_1$–$C_5$alkylene optionally substituted with one or more $C_1$–$C_4$alkyl groups;

V is $C(O)R_8$;

$R_8$ is OH or $OR_{13}$; and $R_{13}$ is $C_1$–$C_6$alkyl, $C_3$–$C_6$alkenyl, $C_3$–$C_6$alkynyl or an alkali metal, alkaline earth metal, ammonium or tri($C_1$–$C_6$alkyl)ammonium cation.

More preferred formula I herbicidal agents of the present invention are those having the structural formula II

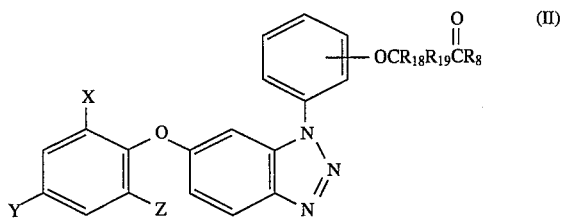

wherein

X is hydrogen, halogen or $CF_3$;

Y and Z are each independently halogen or $CF_3$;

$R_8$ is OH or $OR_{13}$;

$R_{13}$ is $C_1$–$C_4$alkyl or an alkali metal, alkaline earth metal, ammonium or tri($C_1$–$C_6$alkyl)ammonium cation; and $R_{18}$ and $R_{19}$ are each independently hydrogen or $C_1$–$C_4$alkyl.

Aryloxy-N-(substituted phenyl)benzotriazole compounds of the present invention which are particularly effective herbicidal agents include methyl 2-{o-{6-[(2-chloro-α,α,α,6-tetrafluoro-p-tolyl)oxy]-1H-benzotriazol-1-yl}phenoxy}propionate;

{o-{6-[(2-chloro-α,α,α,6-tetrafluoro-p-tolyl)oxy]-1H-benzotriazol-1-yl}phenoxy}acetic acid;

{o-{[6-(2-chloro-α,α,α-trifluoro-p-tolyl)oxy]-1H-benzotriazol-1-yl}phenoxy}acetic acid;

sodium {o-{6-[(2-chloro-α,α,α,6-tetrafluoro-p-tolyl)oxy]-1H-benzotriazol-1-yl}phenoxy}acetate;

methyl {o-{6-[(2-chloro-α,α,α-trifluoro-p-tolyl)oxy]-1H-benzotriazol-1-yl}phenoxy}acetate;

{o-[6-(2,4-dichlorophenoxy)-1H-benzotriazol-1-yl]phenoxy}acetic acid;

methyl {o-{6-[(2-chloro-α,α,α,6-tetrafluoro-p-tolyl)oxy]-1H-benzotriazol-1-yl}phenoxy}acetate; and methyl 2-{p-{6-[(2-chloro-α,α,α,6-tetrafluoro-p-tolyl)oxy]-1H-benzotriazol-1-yl}phenoxy}propionate, among others.

Exemplary of halogen hereinabove are fluorine, chlorine, bromine and iodine. The term $C_1$–$C_4$haloalkyl as used in the specification and claims designates a $C_1$–$C_4$alkyl group substituted with one or more halogen atoms. In formulas I and II above, alkali metals include: sodium, potassium and lithium. Alkaline earth metals of formulas I and II include magnesium and calcium. Further, the term organic ammonium is defined as a group consisting of a positively charged nitrogen atom joined to from one to four aliphatic groups, each containing from one to sixteen carbon atoms.

It has now been found that the compounds of the present invention are especially useful for the postemergence control of undesirable plant species.

Compounds of formula I wherein W is O, m is 1 and V is $CO_2R_{13}$ may be prepared by reacting a dinitrophenyl compound of formula III with an aniline compound of formula IV at an elevated temperature to form a N-(2-nitro-5-aryloxyphenyl)anisidine compound of formula V, reducing the formula V compound with iron in the presence of an organic acid such as acetic acid, preferably at an elevated temperature, to form a N-(2-amino-5-aryloxyphenyl)anisidine compound of formula VI, cyclizing the formula VI compound with sodium nitrite in an acetic acid solution to form an aryloxy-1-(methoxyphenyl)benzotriazole compound of formula VII, reacting the formula VII compound with boron tribromide to form an (aryloxy-1H-benzotriazol-1-yl)phenol compound of formula VIII, and reacting the formula VIII compound with a substituted ester of formula IX in the presence of a base such as potassium carbonate to form the desired compound. The above reactions are shown in Flow Diagram I.

FLOW DIAGRAM I

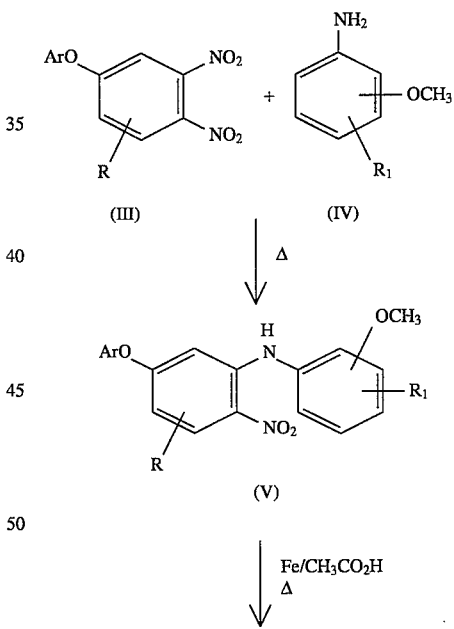

-continued
FLOW DIAGRAM I

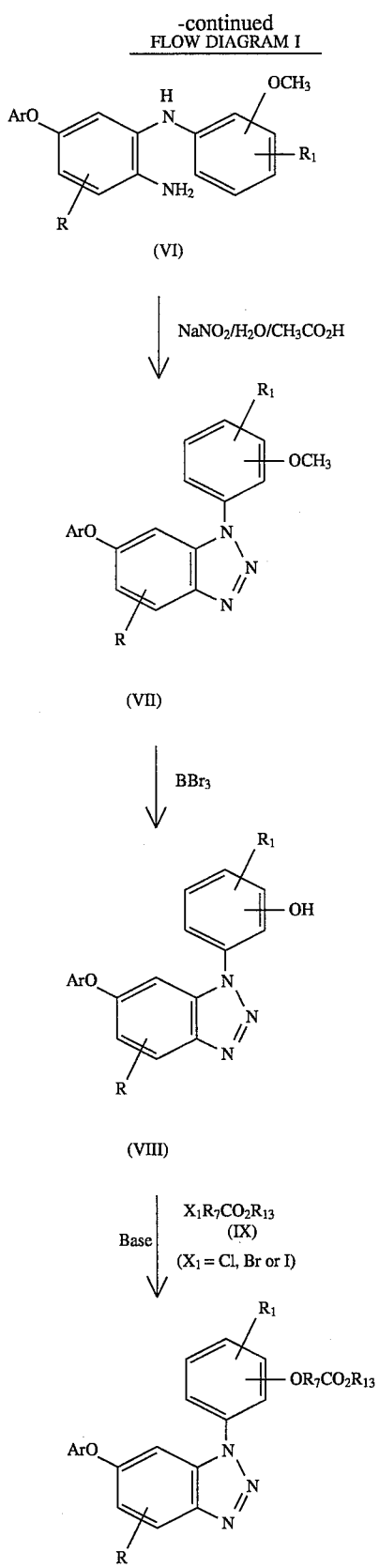

Alternatively N-(2-nitro-5-aryloxyphenyl)anisidine compounds of formula V may be prepared by reacting a 2,4-difluoronitrophenyl compound of formula X with the aniline compound of formula IV in the presence of a base such as potassium carbonate to form a N-(5-fluoro-2-nitrophenyl)anisidine compound of formula XI, and reacting the formula XI compound with an alcohol of formula XII in the presence of a base such as potassium carbonate to form the desired formula V compound. The above reaction scheme is shown in Flow Diagram II.

FLOW DIAGRAM II

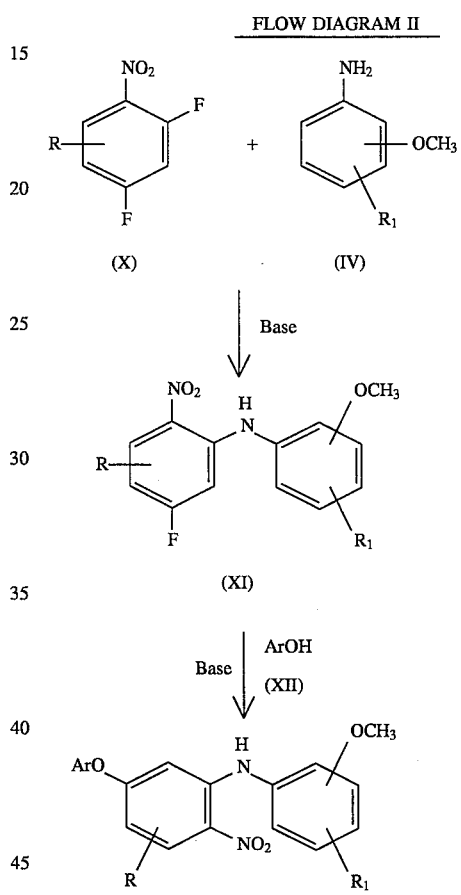

Similarly, certain formula I compounds wherein W is S, m is 1 and V is $CO_2R_{13}$ may be prepared by reacting the 2,4-difluoronitrophenyl compound of formula X with a substituted aniline compound of formula XIII in the presence of a base to form a N-(5-fluoro-2-nitrophenyl)anisidine compound of formula XIV, reacting the formula XIV compound with the alcohol of formula XII in the presence of a base to form a N-(2-nitro-5-aryloxyphenyl)anisidine compound of formula XV, reducing the formula XV compound with iron in the presence of an organic acid such as acetic acid, preferably at an elevated temperature, to form a N-(2-amino-5-aryloxyphenyl)anisidine compound of formula XVI, and cyclizing the formula XVI compound with sodium nitrite in an acetic acid solution. The reaction scheme is shown below in Flow Diagram III.

FLOW DIAGRAM III

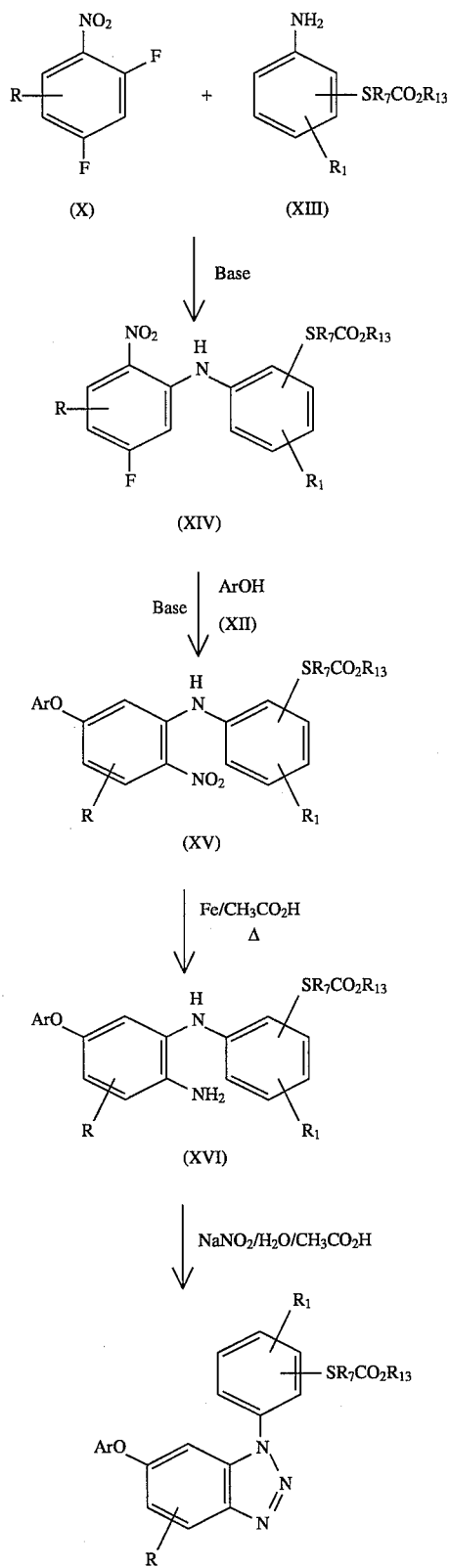

Compounds of formula I wherein W is $NR_6$, m is 1 and V is $CO_2R_{13}$ may be prepared by reacting an amine of formula XVII with the substituted ester of formula IX to form an amino-ester compound of formula XVIII, reducing the formula XVIII compound with iron in the presence of an organic acid such as acetic acid to form a formula XIX compound, reacting the formula XIX compound with the 2,4-difluoronitrophenyl compound of formula X in the presence of a base to form a formula XX compound, reacting the formula XX compound with the alcohol of formula XII in the presence of a base to form a formula XXI compound, reducing the formula XXI compound with iron in the presence of an organic acid such as acetic acid to form a formula XXII compound, cyclizing the formula XXII compound with sodium nitrite in an acetic acid solution to form a compound of formula XXIII, and reacting the formula XXIII compound with aluminum chloride to form the desired compound wherein $R_6$ is hydrogen and optionally alkylating the compound wherein $R_6$ is hydrogen with an alkylhalide of formula XXIV in the presence of a base to form the desired compound wherein $R_6$ is $C_1$–$C_4$alkyl. The above reactions are shown in Flow Diagram IV.

FLOW DIAGRAM IV

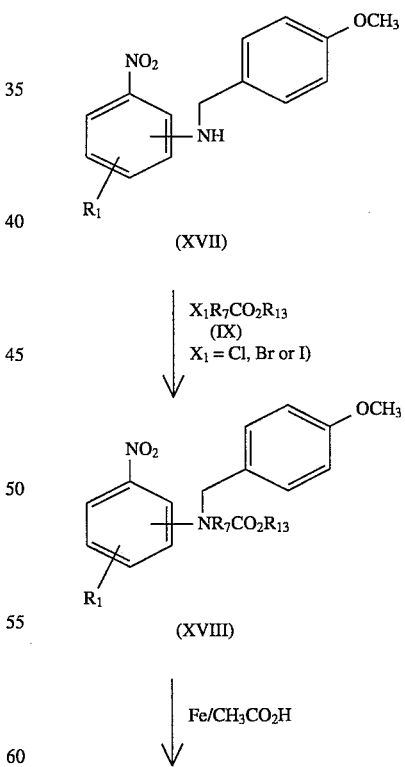

-continued
FLOW DIAGRAM IV
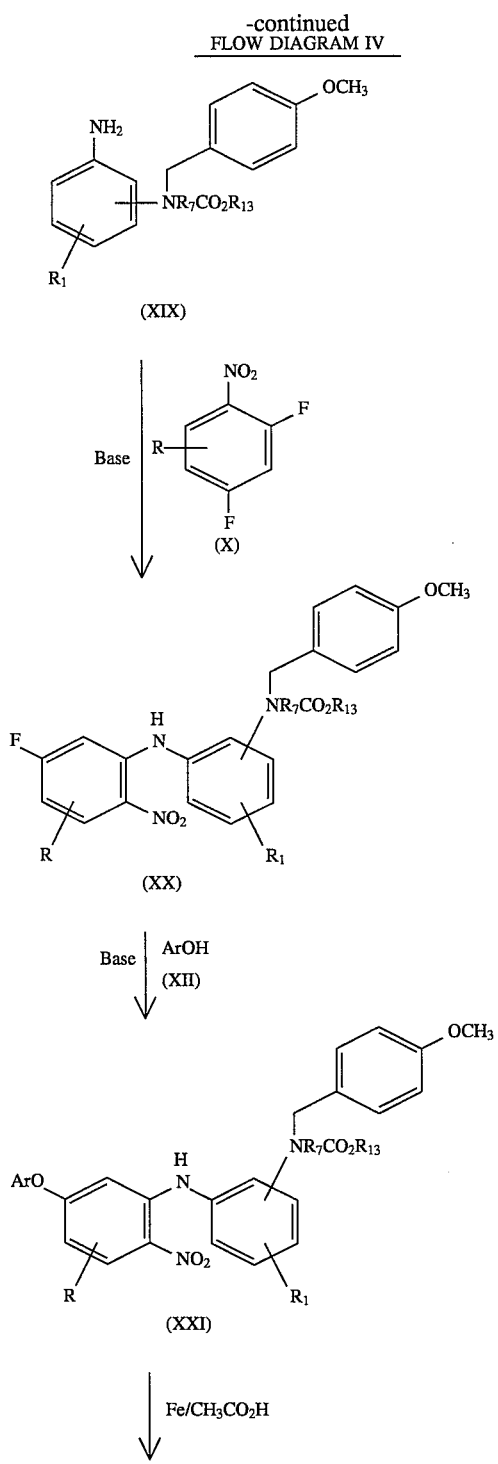
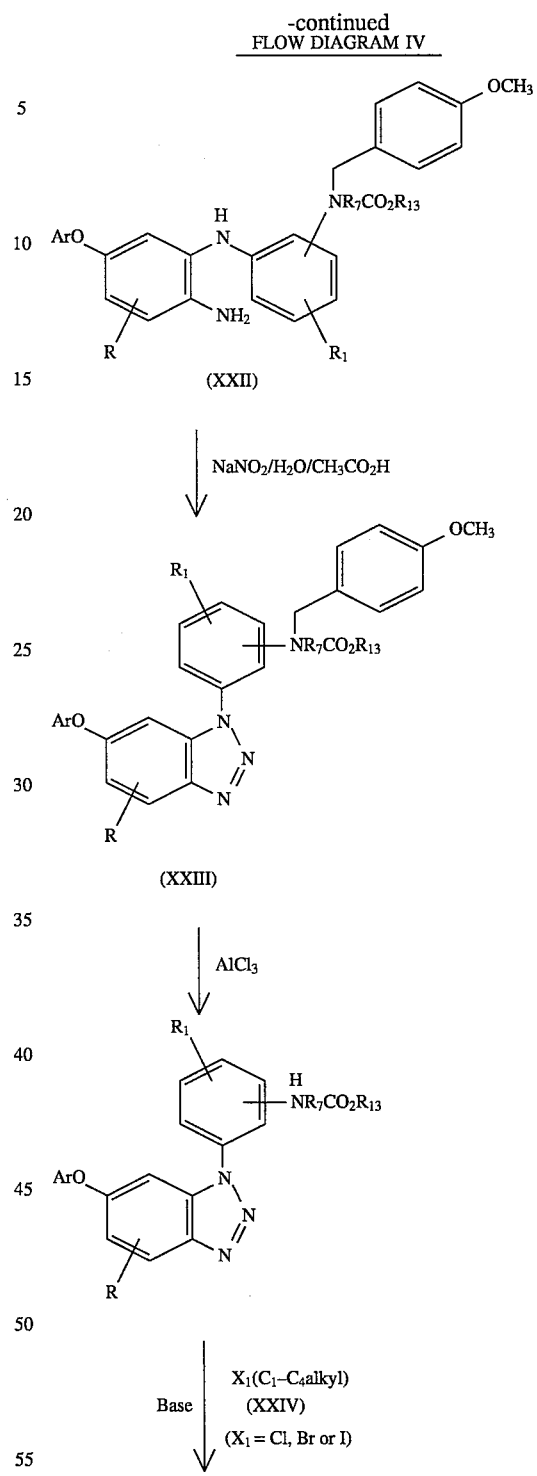

-continued
FLOW DIAGRAM IV

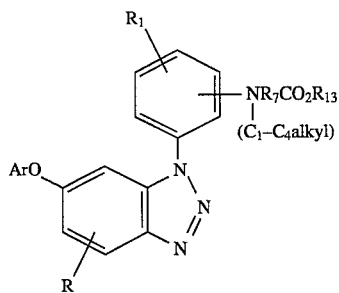

Formula I compounds wherein m is 0 and V is $CO_2R_{13}$ may be prepared by reacting the 2,4-difluoronitrophenyl compound of formula X with a substituted aniline of formula XXV in the presence of a base to form a formula XXVI compound, reacting the formula XXVI compound with the alcohol of formula XII in the presence of a base to form a formula XXVII compound, reducing the formula XXVII compound with iron in the presence of an organic acid such as acetic acid to form a formula XXVIII compound, and cyclizing the formula XXVIII compound with sodium nitrite in an acetic acid solution. The rections are shown below in Flow Diagram V.

FLOW DIAGRAM V

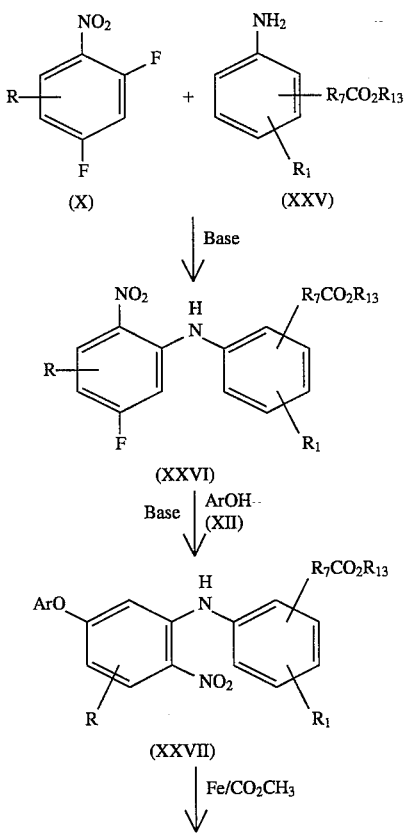

-continued
FLOW DIAGRAM V

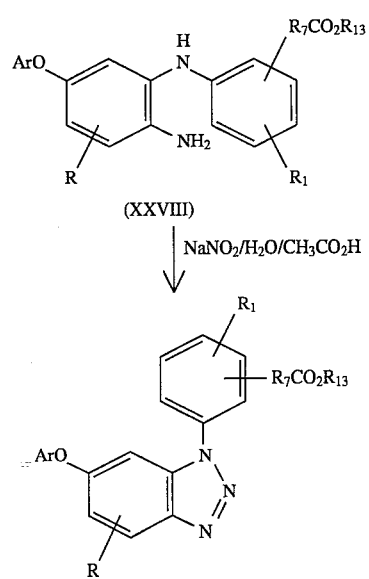

Compounds of formula I wherein $R_8$ is $NR_{14}R_{15}$ may be prepared using standard procedures such as hydrolyzing the appropriate ester of formula XXIX in the presence of a base to form the corresponding acid, reacting the acid with thionyl chloride to give the acid chloride of formula XXX and reacting the formula XXX acid chloride with an amine of formula XXXI optionally in the presence of a base to give the desired product. The reactions are shown below in Flow Diagram VI.

FLOW DIAGRAM VI

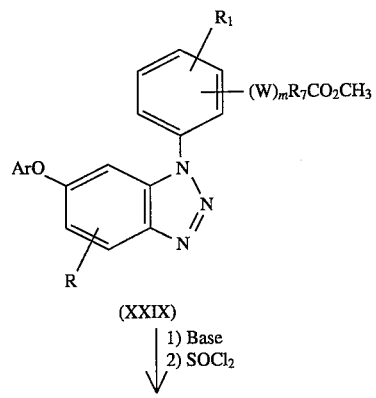

-continued
FLOW DIAGRAM VI

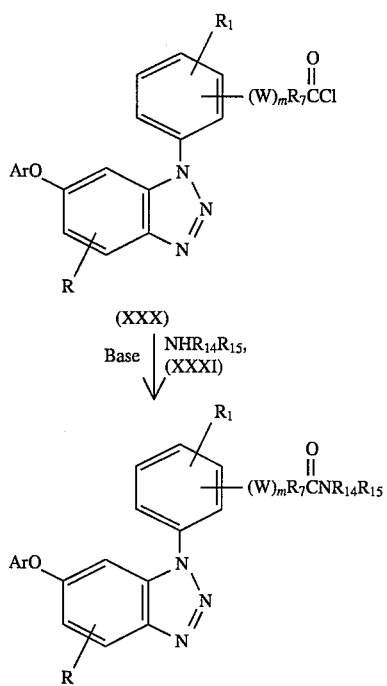

Similarly, certain compounds of formula I wherein $R_8$ is $N(R_9)SO_2R_{12}$ may be prepared by reacting the acid chloride of formula XXX with a sulfonamide of formula XXXII optionally in the presence of a base. The reaction scheme is shown in Flow Diagram VII.

FLOW DIAGRAM VII

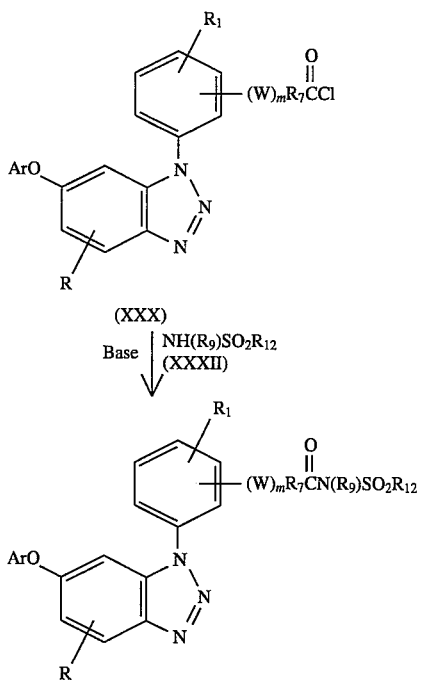

Using the formula XXX acid chloride, formula I compounds wherein V is $C(O)R_9$ may also be prepared as shown below in Flow Diagram VIII.

FLOW DIAGRAM VIII

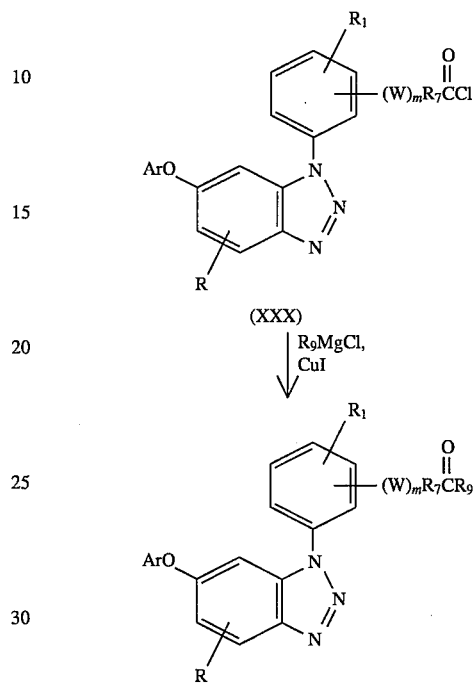

Formula I compounds wherein W is oxygen, m is 1 and V is $CH(OR_{11})_2$, CHO or $HC=NOR_{10}$ may be prepared by reacting the formula VIII compound with an acetal of formula XXXIII in the presence of a base to form the formula XXXIV acetal, reacting the formula XXXIV acetal with acid to form the formula XXXV aldehyde, and reacting the aldehyde with an amine of formula XXXVI. The reactions are shown below in Flow Diagram IX.

FLOW DIAGRAM IX

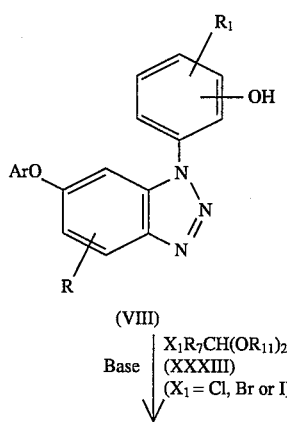

FLOW DIAGRAM IX -continued

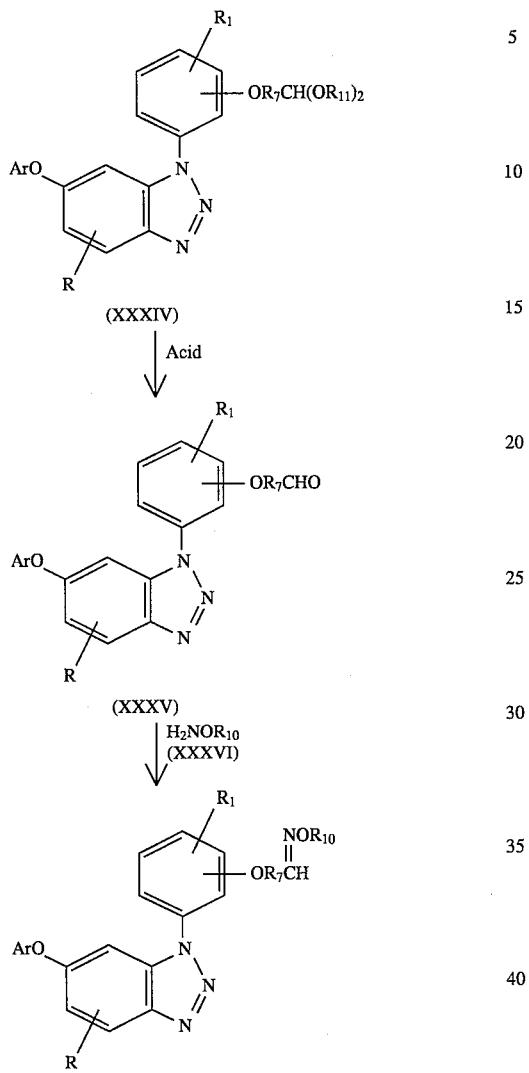

FLOW DIAGRAM X

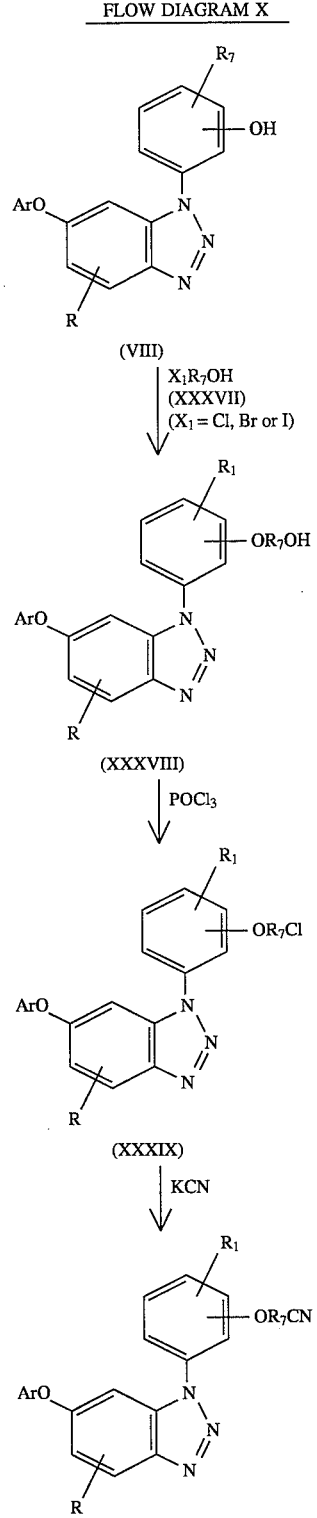

Compounds of formula I wherein V is cyano may be prepared by reacting the formula VIII compound with a haloalcohol of formula XXXVII to give the alcohol of formula XXXVIII, reacting the formula XXXVIII alcohol with phosphorus oxychloride to give the chloride compound of formula XXXIX, and reacting the chloride compound with potassium cyanide to obtain the desired compound. The reaction sequence is shown below in Flow Diagram X.

Using the formula XXXVIII alcohol, formula I compounds wherein $R_9$ is $C_1$–$C_4$alkyl optionally substituted with $C_1$–$C_4$alkoxy may be prepared as shown below in Flow Diagram XI.

FLOW DIAGRAM XI

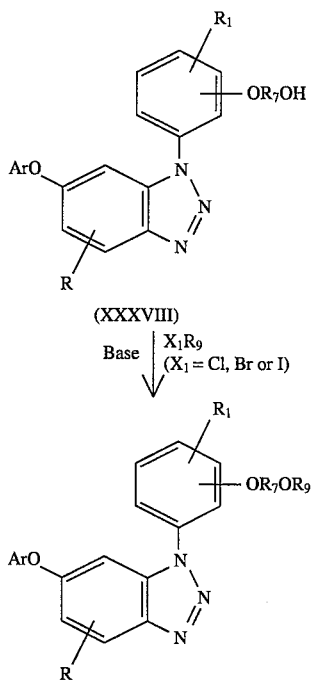

(XXXVIII)

Similarly, compounds of formula I wherein $R_{10}$ is $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups may be prepared by reacting a formula XXXVIII alcohol with an acid chloride of formula XL in the presence of a base. The reaction is shown in Flow Diagram XII.

FLOW DIAGRAM XII

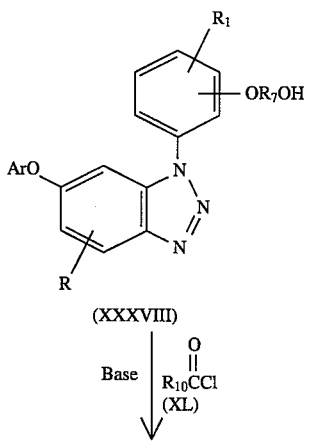

(XXXVIII)

-continued
FLOW DIAGRAM XII

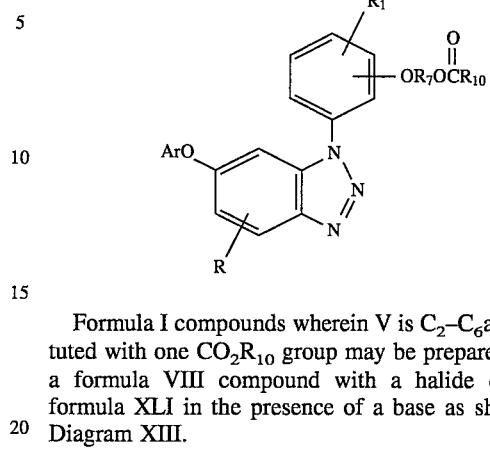

Formula I compounds wherein V is $C_2$–$C_6$alkenyl substituted with one $CO_2R_{10}$ group may be prepared by reacting a formula VIII compound with a halide compound of formula XLI in the presence of a base as shown in Flow Diagram XIII.

FLOW DIAGRAM XIII

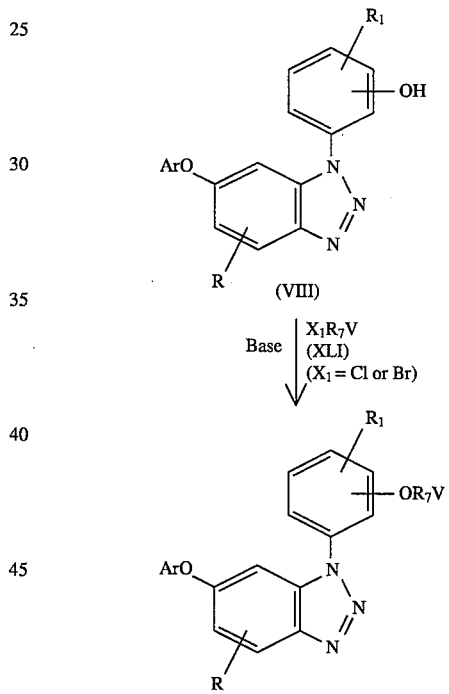

Formula I compounds wherein $R_8$ is hydroxy may be prepared by hydrolyzing a formula XLII ester in the presence of a base followed by treatment with acid as shown in Flow Diagram XIV.

FLOW DIAGRAM XIV

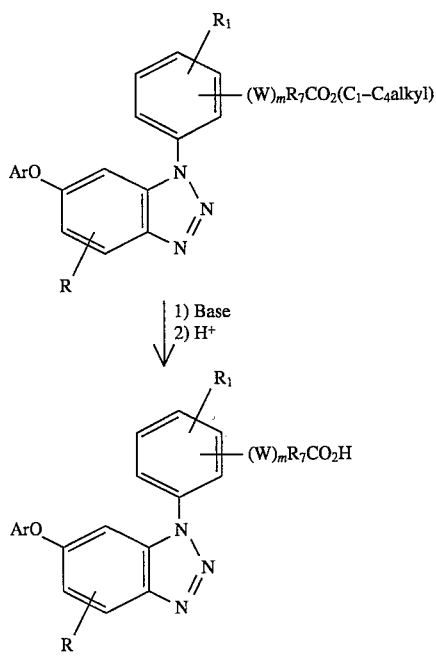

1) Base
2) H+

Advantageously, formula I compounds wherein $R_{13}$ is an alkali metal, alkaline earth metal, manganese, copper, zinc, cobalt, silver, nickel, ammonium or organic ammonium cation may be prepared from formula I compounds wherein $R_8$ is OH by conventional processes known to those skilled in the art.

The formula I aryloxy-N-(substituted phenyl)benzotriazole compounds of the present invention are effective herbicidal agents useful for the control of a wide variety of undesirable plant species. Those compounds are effective for controlling weeds native to both dry land and wet land areas. The compounds are also useful as aquatic herbicides and are effective in controlling the above-said plants when applied to the foliage thereof or to soil or water containing seeds or other propagating organs thereof such as stolons, tubers or rhizomes, at rates of from about 0.016 kg/ha to 4 kg/ha and preferably from about 0.05 kg/ha to 2 kg/ha.

The compounds of this invention are best suited for use as broad spectrum herbicides, especially when applied postemergence to the locus in which weed control is desired. However, certain compounds of this invention are selective. In fact, some of the compounds of this invention are selective in crops such as soybeans, corn and rice.

While the compounds of this invention are effective for controlling undesirable plant species when employed alone, they may also be used in combination with other biological chemicals, including other herbicides.

The formula I compounds of this invention may be applied to crops in the form of a solid or liquid herbicidal composition, comprising a herbicidally effective amount of the formula I compound dispersed or dissolved in an agronomically acceptable, inert solid or liquid carrier. The compositions may be applied as preemergence or postemergence treatments.

Advantageously, the formula I compounds may be formulated as emulsifiable concentrates, wettable powders, granular formulations, flowable concentrates and the like.

In order to facilitate a further understanding of the invention, the following examples are presented primarily for the purpose of illustrating more specific details thereof. The invention should not be deemed limited by the examples as the full scope of the invention is defined in the claims. The term NMR designates nuclear magnetic resonance spectroscopy.

EXAMPLE 1

Preparation of 2-Chloro-α,α,α,6-tetrafluoro-p-tolyl m-nitrophenyl ether

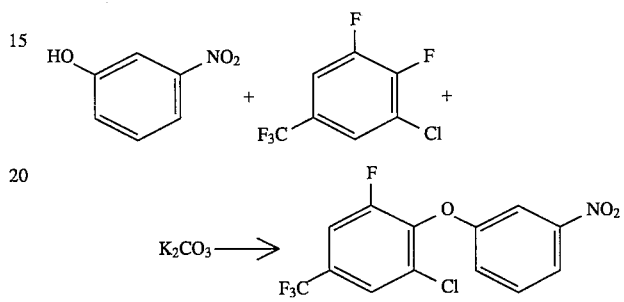

A mixture of 3-nitrophenol (50.0 g, 0.359 mol), potassium carbonate (56.4 g, 0.408 mol) and 3-chloro-4,5-difluorobenzotrifluoride (77.7 g, 0.359 mol) in methyl sulfoxide is heated at 100° C. for 5.5 hours, cooled to and held at room temperature for 12 hours and poured into water. The resulting aqueous mixture is extracted with ether. The organic extracts are combined, washed sequentially with water and brine, dried over anhydrous magnesium sulfate and concentrated in vacuo to obtain an orange oil. Flash column chromatography of the oil using silica gel and dichloromethane/petroleum ether solutions gives the title product as a yellow oil (105.5 g, 87.6%) which is identified by NMR spectral analyses.

EXAMPLE 2

Preparation of 2-Chloro-α,α,α,6-tetrafluoro-p-tolyl 3,4-dinitrophenyl ether

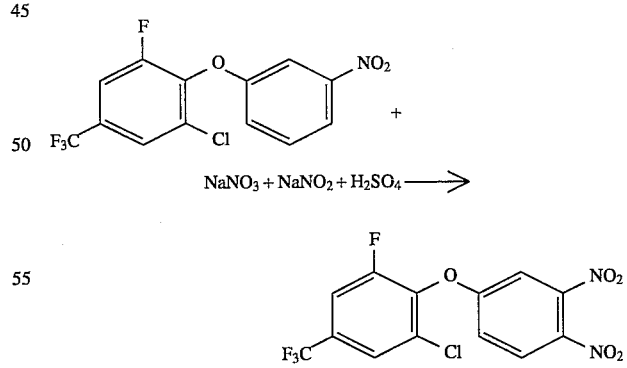

Sodium nitrite (0.22 g, 0.0032 mol) is added to a mixture of sodium nitrate (24.8 g, 0.292 mol) in concentrated sulfuric acid (165 mL) at 10° C. To the resultant mixture, a solution of 2-chloro-α,α,α,6-tetrafluoro-p-tolyl m-nitrophenyl ether (54.3 g, 0.162 mol) in chloroform is added over a 5 minute period at 10° C. After the addition is complete, the reaction mixture is warmed to and stirred at room temperature for 3 days. The sulfuric acid layer is separated and extracted with dichloromethane. The organic layers are combined, washed sequentially with brine and dilute sodium hydrogen carbonate solution, dried over anhydrous magnesium sulfate and concentrated in vacuo to obtain an orange oil. Chromatography of the oil using silica gel and a 1:1 dichloromethane/petroleum ether solution gives the title product as a pale yellow oil (60.8 g, 98.5%) which is identified by NMR spectral analyses.

EXAMPLE 3

Preparation of N-{5-[(2-Chloro-α,α,α,6-tetrafluoro-p-tolyl)oxy]-2-nitrophenyl}-o-anisidine

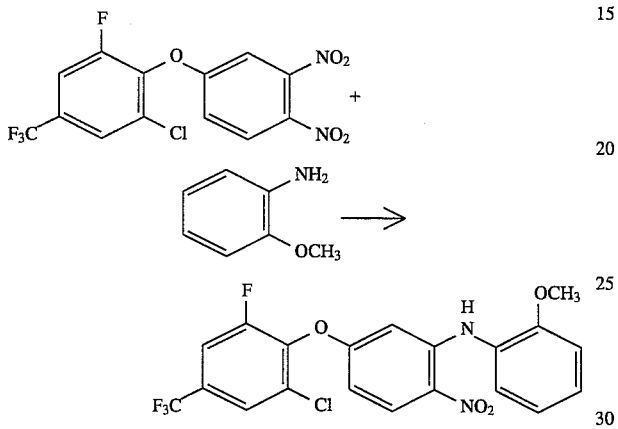

A solution of 2-chloro-α,α,α,6-tetrafluoro-p-tolyl 3,4-dinitrophenyl ether (20.0 g, 0.0525 mol) and o-anisidine (12.9 g, 0.105 mol) in acetonitrile is stirred overnight at 50° C., treated with additional o-anisidine (0.65 g), stirred overnight at 50° C., treated with additional o-anisidine (1.62 g), stirred for 3 days at 50° C., refluxed for 4 days, cooled and poured into water. The aqueous mixture is extracted with ethyl acetate. The organic extract is washed sequentially with water and brine, dried over anhydrous magnesium sulfate and concentrated in vacuo to obtain a black oil. Flash column chromatography of the oil using silica gel and dichloromethane/petroleum ether solutions gives the title product as an orange oil (14.5 g, 60.4%) which is identified by NMR spectral analyses.

EXAMPLE 4

Preparation of N-{2-Amino-5-[(2-chloro-α,α,α, 6-tetrafluoro-p-tolyl)oxy]phenyl}-o-anisidine

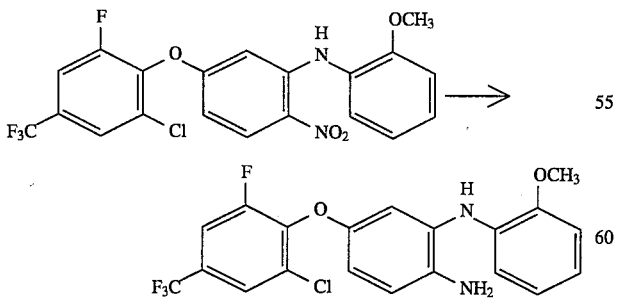

A solution of N-{5-[(2-chloro-α,α,α,6-tetrafluoro-p-tolyl)oxy]-2-nitrophenyl}-o-anisidine (14.5 g, 0.0317 mol) in ethyl acetate is added to a mixture of iron (7.1 g, 0.127 mol) in 5% acetic acid at 65° C. The reaction mixture is stirred at 65° C. for 2 hours, treated with additional iron (1.77 g), stirred at 65° C. for 1 hour, cooled and filtered through diatomaceous earth. The filtrate is extracted with ethyl acetate and the organic extract is washed sequentially with water and brine, dried over anhydrous magnesium sulfate and concentrated in vacuo to give a dark oil. Flash column chromatography of the oil using silica gel and dichloromethane gives the title product as a dark oil (10.5 g, 77.8%) which is identified by NMR spectral analyses.

EXAMPLE 5

Preparation of 6-[(2-Chloro-α,α,α,6-tetra-fluoro-p-tolyl)oxy]-1-(o-methoxyphenyl)-1H-benzotriazole

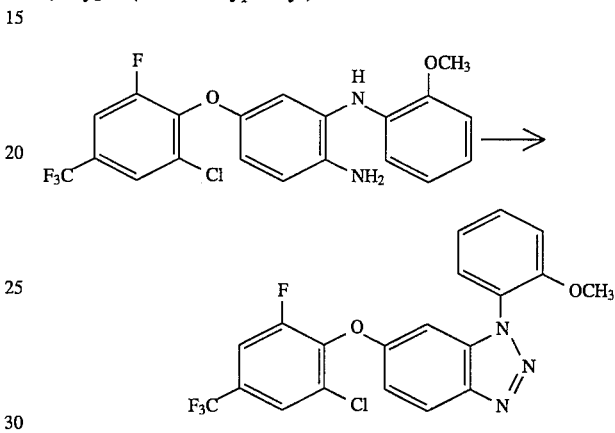

A solution of N-{2-amino-5-[(2-chloro-α,α,α,6-tetrafluoro-p-tolyl)oxy]phenyl}-o-anisidine (10.0 g, 0.0234 mol) in tetrahydrofuran is added to a 1:1 acetic acid/water solution at 0° C. A solution of sodium nitrite (3.39 g, 0.0491 mol) in water is then slowly added to the resultant mixture over a 30 minute period at 0° C. After the addition, the reaction mixture is warmed to and stirred at room temperature overnight and poured into water. The aqueous mixture is extracted with ethyl acetate and the organic extract is washed sequentially with water and brine, dried over anhydrous magnesium sulfate and concentrated in vacuo to obtain a dark oil. Flash column chromatography of the oil using silica gel and dichloromethane gives the title product as a brown solid (8.8 g, 86.3%, mp 116–118° C.).

Using essentially the same procedure, the following compounds are obtained:

| X | Y | Z | mp °C. |
|---|---|---|---|
| Cl | Cl | H | 95–99 |
| H | CF₃ | Cl | 110.5–114 |

EXAMPLE 6

Preparation of o-{6-[(2-Chloro-α,α,α,6-tetra-fluoro-p-tolyl)oxy]-1H-benzotriazol1-yl}phenol

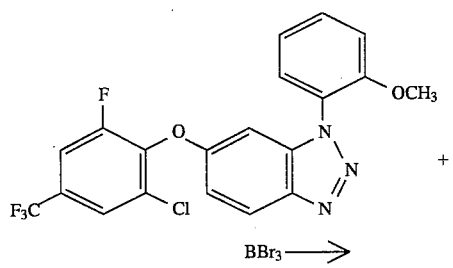

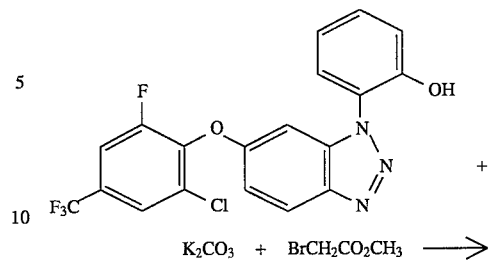

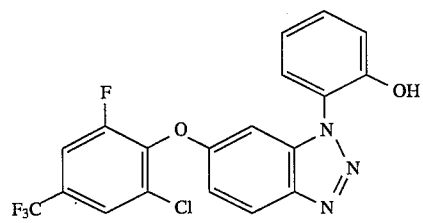

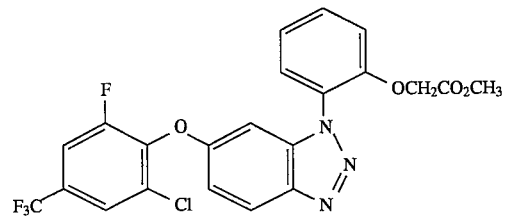

A solution of 6-[(2-chloro-α,α,α,6-tetrafluoro-p-tolyl)oxy]-1-(o-methoxyphenyl)-1H-benzotriazole (8.75 g, 0.020 mol) in dichloromethane is slowly added to 40 mL of a 1M boron tribromide in dichloromethane solution while maintaining the reaction mixture temperature below −16°. After the addition, the reaction mixture is warmed to and stirred at room temperature overnight and poured onto ice. The aqueous mixture is extracted with dichloromethane and the organic extract is dried over anhydrous magnesium sulfate and concentrated in vacuo to obtain a brown solid. Flash column chromatography of the solid using silica gel and dichloromethane/ethyl acetate solutions gives the title product as an off-white solid, mp 162–163° C.

Using essentially the same procedure, the following compounds are obtained:

A mixture of o-{6-[(2-chloro-α,α,α,6-tetrafluoro-p-tolyl)oxy]-1H-benzotriazol-1-yl}phenol (1.00 g, 2.36 mmol), potassium carbonate (0.50 g, 3.62 mmol) and methyl bromoacetate (0.44 g, 2.88 mmol) in N,N-dimethylformamide is stirred at room temperature for 4 hours and poured into water. The resulting aqueous mixture is extracted with ethyl acetate and the organic extract is washed sequentially with water and brine, dried over anhydrous magnesium sulfate and concentrated in vacuo to obtain a pale yellow oil. Flash column chromatography of the oil using silica gel and a 40:1 dichloromethane/ethyl acetate solution gives the title product as a white solid (1.07 g, 89.9%, mp 118–119° C.).

Using essentially the same procedure, the following compounds are obtained:

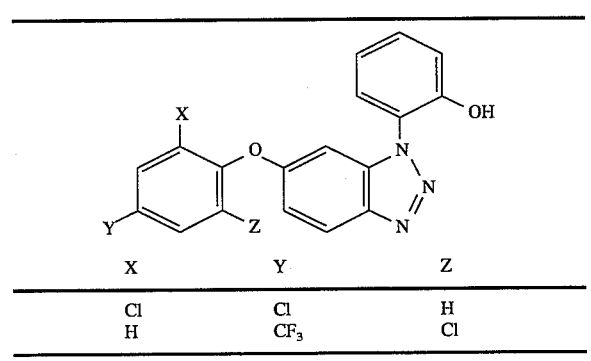

| X | Y | Z |
|---|---|---|
| Cl | Cl | H |
| H | CF$_3$ | Cl |

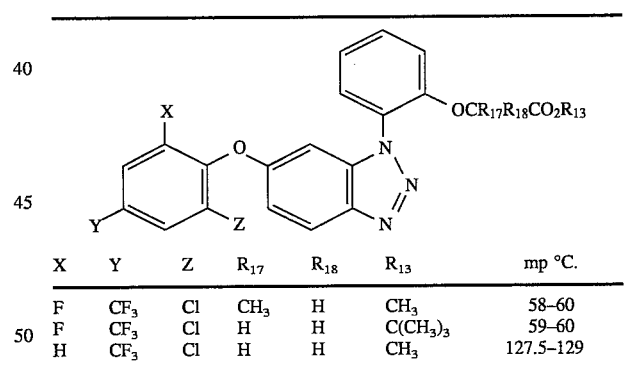

| X | Y | Z | R$_{17}$ | R$_{18}$ | R$_{13}$ | mp °C. |
|---|---|---|---|---|---|---|
| F | CF$_3$ | Cl | CH$_3$ | H | CH$_3$ | 58–60 |
| F | CF$_3$ | Cl | H | H | C(CH$_3$)$_3$ | 59–60 |
| H | CF$_3$ | Cl | H | H | CH$_3$ | 127.5–129 |

EXAMPLE 8

Preparation of {o-{6-[(2-Chloro-α,α,α,6-tetrafluoro-p-tolyl)oxy]-1H-benzotriazol-1-yl}phenoxy}acetic acid

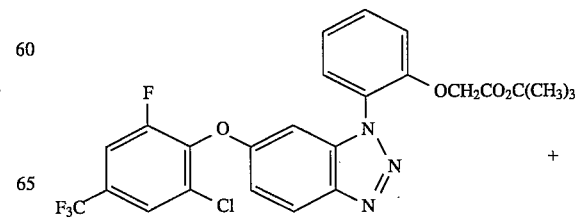

EXAMPLE 7

Preparation of Methyl {o-{6-[(2-Chloro-α,α,α,6-tetrafluoro-p-tolyl)oxy]-1H-benzotriazol-1-yl}phenoxy}acetate -continued

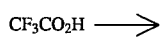

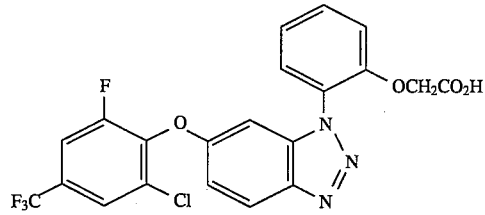

Trifluoroacetic acid (10 mL) is added to a solution of tert-butyl {o-{6-[(2-chloro-α,α,α,6-tetra-fluoro-p-tolyl)oxy]- 1H-benzotriazol-1-yl}phenoxy}acetate (1.90 g, 3.53 mmol) in dichloromethane. The reaction mixture is stirred at room temperature for 2 hours and concentrated in vacuo to give the title product as an off-white foam (1.69 g, 100%, mp 212–213° C.).

EXAMPLE 9

Preparation of Sodium {o-{6[(2-chloro-α,α,α,6-tetrafluoro-p-tolyl)oxy]-1H-benzotriazol-1-yl}phenoxy}acetate

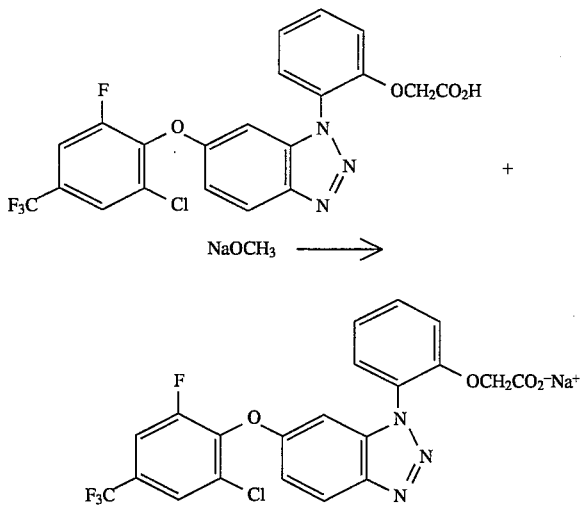

A solution of sodium (0.069 g, 3.00 mmol) in methanol (5 mL) is added to a mixture of {o-{6-[(2-chloro-α,α,α, 6-tetrafluoro-p-tolyl) oxy]-1H-benzotriazol-1-yl}phenoxy}acetic acid (1.40 g, 2.91 mmol) in methanol. The reaction mixture is stirred for 15 minutes and concentrated in vacuo to give the title product as a yellow solid (1.43 g, 97.9%, mp 210° C. dec.).

EXAMPLE 10

Preparation of N-(5-Fluoro-2-nitrophenyl)-o-anisidine

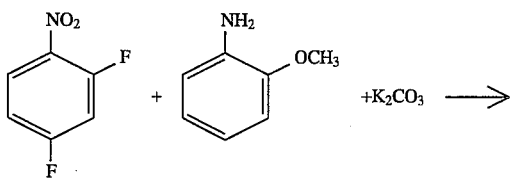

-continued

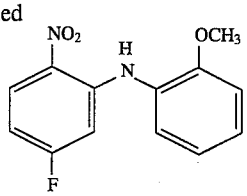

A mixture of 2,4-difluoronitrobenzene (110.0 g, 0.69 mol), 2-methoxyaniline (128.0 g, 1.04 mol) and potassium carbonate (144.0 g, 1.04 mol) in methyl sulfoxide is heated to and stirred at 70–95° C. overnight, stirred at about 50° C. for 24 hours, cooled and diluted with an ice/water mixture. The aqueous mixture is filtered and the filter cake is washed sequentially with water, dilute hydrochloric acid and water and dried to obtain a gum. The gum is dissolved in a 1:1 hexanes/toluene solution and passed through a silica gel pad to give the title prouduct as a solid.

EXAMPLE 11

Preparation of N-[5-(2,4-Dichlorophenoxy)-2-nitrophenyl]-o-anisidine

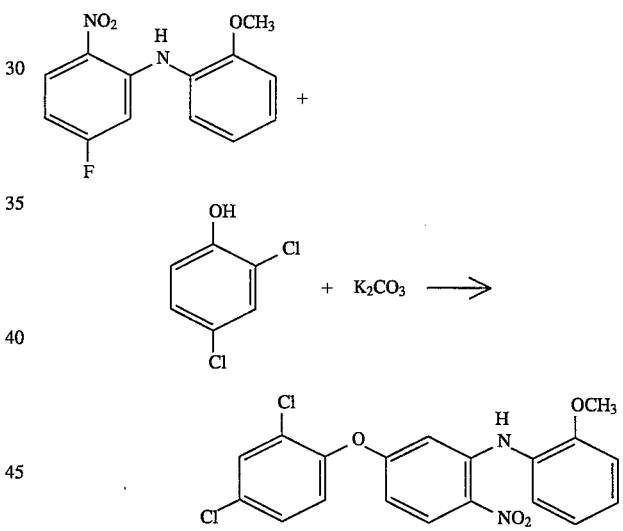

A mixture of N-(5-fluoro-2-nitrophenyl)-o-anisidine (10.25 g, 0.039 mol), 2,4-dichlorophenol (7.0 g, 0.043 mol) and potassium carbonate (13.1 g, 0.095 mol) in methyl sulfoxide is stirred at 90° C. overnight, cooled and diluted with a dichloromethane/water mixture. The organic layer is separated, washed with brine, dried over anhydrous sodium sulfate and concentrated in vacuo to obtain a gum. A mixture of the gum in acetone is concentrated in vacuo to give a yellow solid which is recrystallized from ethanol to give the title product as an orange solid, mp 105–107° C.

Using essentially the same procedure, N-{5-[(2-chloro-α,α,α-trifluoro-p-tolyl)oxy]-2-nitrophenyl}-o-anisidine is obtained.

EXAMPLE 12

Preparation of N-[2-Amino-5-(2,4-dichlorophenoxy)phenyl]-o-anisidine

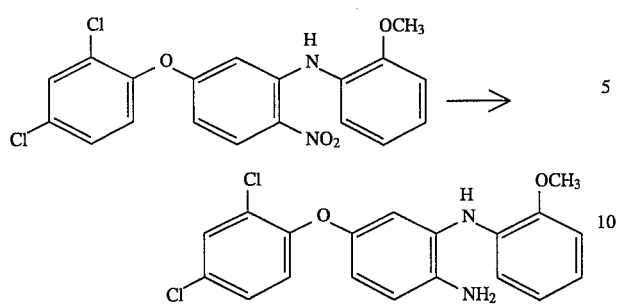

A mixture of N-[5-(2,4-dichlorophenoxy)-2nitrophenyl]-o-anisidine (13.4 g, 0.0331 g) and Raney® nickel (5.7 g) in tetrahydrofuran is hydrogenated until 86.2 psi of hydrogen is used and filtered through diatomaceous earth. The filtrate is concentrated in vacuo to give the title product as a red gum.

Using essentially the same procedure, N-{2-amino-5-[(2-chloro-α,α,α-trifluoro-p-tolyl)oxy]phenyl}-o-anisidine is obtained as a red gum.

EXAMPLE 13

Preparation of {o-[6-(2,4-Dichlorophenoxy-1H-benzotriazol-1-yl]phenoxy}acetic acid

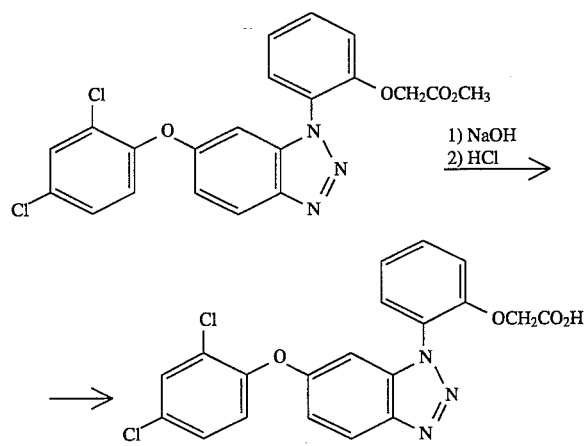

A solution of methyl {o-[6-(2,4-dichlorophenoxy)-1H-benzotriazol-1-yl]phenoxy}acetate (1.9 g, 4.28 mmol) and sodium hydroxide (0.34 g, 8.5 mmol) in a 1:10:2 water/tetrahydrofuran/methanol solution is stirred for 3 hours, acidified with concentrated hydrochloric acid and filtered. The filtrate is concentrated in vacuo to obtain a yellow glass. The glass is recrystallized from a 1:1 tetrahydrofuran/hexanes solution to give the title product as a white solid (1.84 g, mp 157.5–162° C.).

EXAMPLE 14

Preparation of Methyl 2-{p-{5-[(2-chloro-α,α,α,6-tetrafluoro-p-tolyl)oxy]2-nitroanilino}phenoxy}propionate

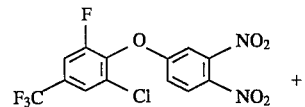 +

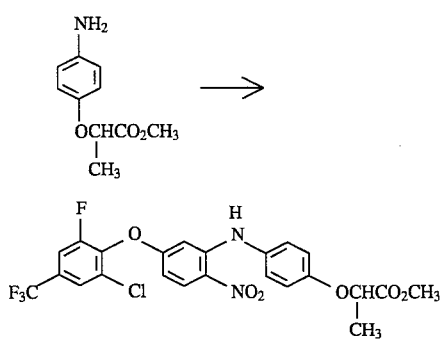

A solution of 2-chloro-α,α,α,6-tetrafluoro-p-tolyl 3,4-dinitrophenyl ether (15.6 g, 0.041 mol) and methyl 2-(4-aminophenoxy)propionate (16.0 g, 0.082 mol) in dioxane is refluxed for 4 hours, cooled to room temperature and poured into water. The aqueous mixture is extracted with ethyl acetate. The organic extracts are combined, washed sequentially with brine and water, dried over anhydrous sodium sulfate and concentrated in vacuo to obtain a black tar. Flash column chromatography of the tar using silica gel and a 1:4 hexanes/dichloromethane solution gives the title prouct as an orange oil which is identified by NMR spectral analyses.

EXAMPLE 15

Preparation of Methyl 2-{p-{2-amino-5-[(2-chloro-α,α,α,6-tetrafluoro-p-tolyl)oxy]anilino}phenoxy}propionate

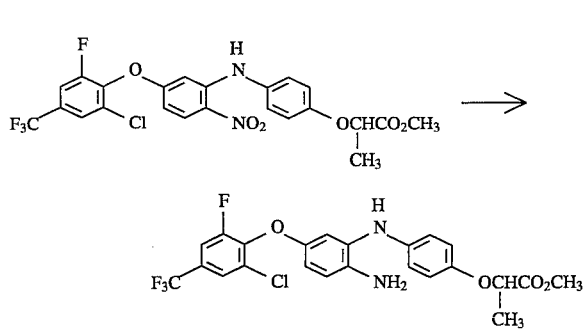

A solution of methyl 2-{p-{5-[2-chloro-α,α,α,6-tetrafluoro-p-tolyl)oxy]-2-nitroanilino}-phenoxy}propionate (3.35 g, 0.0063 mol) in ethyl acetate is added to a mixture of iron (1.06 g, 0.019 mol) in a 5% acetic acid solution at 65° C. for 1 hour and filtered through diatomaceous earth. The filtrate is extracted with ethyl acetate. The organic extracts are combined, washed sequentially with saturated sodium hydrogen carbonate solution and brine, dried over anhydrous sodium sulfate and concentated in vacuo to give the title product as a brown oil which is identified by $^1$HNMR spectral analysis.

EXAMPLE 16

Preparation of Methyl 2-{p-{6-[(2-chloro-α,α,α,6-tetrafluoro-p-tolyl)oxy]-1H-benzotriazol-1-yl}phenoxy}propionate

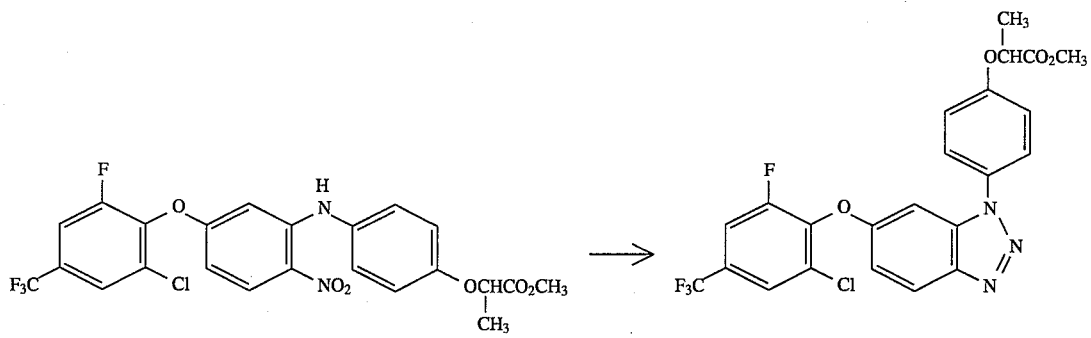

A solution of methyl 2-{p-{2-amino-5-[(2-chloro-α,α,α,6-tetrafluoro-p-tolyl)oxy]anilino}phenoxy}propionate (2.55 g, 0.0051 mol) in tetrahydrofuran is added to a 50% acetic acid solution at 0° C. To the resulting mixture, a solution of sodium nitrite (0.74 g, 0.0107 mol) in water is added. The reaction mixture is warmed to and stirred at room temperature for 3 days and poured into water. The aqueous mixture is extracted with ethyl acetate. The organic extracts are combined, washed sequentially with saturated sodium hydrogen carbonate solution and brine, dried over anhydrous sodium sulfate and concentrated in vacuo to obtain a brown oil. Column chromatography of the oil using silica gel and a 2:3 ether/hexanes solution gives the title product as a beige solid (0.7 g, mp 125–127° C.).

EXAMPLE 17

Preemergence herbicidal evaluation of test compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.125 to 0.500 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this preemergence herbicidal evaluation and in the postemergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

| PLANT SPECIES EMPLOYED IN HERBICIDAL EVALUATIONS | | |
|---|---|---|
| Header Abb. | Common Name | Scientific Name |
| ABUTH | VELVETLEAF | *ABUTILON THEOPHRASTI*, MEDIC. |
| AMARE | PIGWEED, REDROOT | *AMARANTHUS RETROFLEXUS*, L. |
| AMBEL | RAGWEED, COMMON | *AMBROSIA ARTEMISIIFOLIA*, L. |
| CASOB | SICKLEPOD | *CASSIA OBTUSIFOLIA*, L. |
| CHEAL | LAMBSQUARTERS, COMMON | *CHENOPODIUM ALBUM*, L. |
| GALAP | GALIUM | *GALIUM APARINE* |

-continued

| PLANT SPECIES EMPLOYED IN HERBICIDAL EVALUATIONS | | |
|---|---|---|
| Header Abb. | Common Name | Scientific Name |
| IPOHE | MORNINGGLORY, IVYLEAF | *IPOMOEA HEDERACEA*, (L) JACQ. |
| DIGSA | CRABGRASS, (HAIRY) L | *DIGITARIA SANGUINALIS*, (L) SCOP |
| ECHCG | BARNYARDGRASS | *ECHINOCHLOA CRUS-GALLI-* (L) BEAU |
| SETVI | FOXTAIL, GREEN | *SETARIA VIRIDIS*, (L) BEAUV |
| GLXMAW | SOYBEAN, WILLIAMS | *GLYCINE MAX* (L) MERR. CV.WILLIAMS |
| ORYSA | RICE, UNSPECIFIED | *ORYZA SATIVA* L. UNSPECIFIED |
| ZEAMX | CORN, FIELD | *ZEA MAYS* L. (SAMMEL-BEZEICHNUNG) |

| COMPOUNDS EVALUATED AS HERBICIDAL AGENTS | |
|---|---|
| Compound Number | |
| 1 | Methyl 2-{p-{6-[(2-chloro-α,α,α,6-tetrafluoro-p-tolyl)oxy]-1H-benzotriazol-1-yl}phenoxy}-propionate |
| 2 | Methyl {o-{[(2-chloro-α,α,α,6-tetrafluoro-p-tolyl)oxy]-1H-benzotriazol-1-yl}phenoxy}-acetate |
| 3 | Methyl 2-{o-{6-[(2-chloro-α,α,α,6-tetrafluoro p-tolyl)oxy]-1H-benzotriazol-1-yl}phenoxy}-propionate |
| 4 | Methyl {o-[6-(2,4-dichlorophenoxy)-1H-benzotriazol-1-yl]phenoxy}acetate |
| 5 | Methyl {o-{6-[(2-chloro-α,α,α-trifluoro-p-tolyl)oxy]-1H-benzotriazol-1-yl}phenoxy}-acetate |
| 6 | Methyl 2-{o-[6-(2,4-dichlorophenoxy(-1H-benzotriazol-1-yl]phenoxy}propionate |
| 7 | {o-{[6-(2-chloro-α,α,α-trifluoro-p-tolyl)oxy]-1H-benzotriazol-1-yl}phenoxy}acetic acid |
| 8 | {o-[6-(2,4-dichlorophenoxy)-1H-benzotriazol-1-yl]phenoxy}acetic acid |
| 9 | {o{6-[(2-chloro-α,α,α,6-tetrafluoro-p-tolyl)-oxy]-1H-benzotriazol-1-yl}phenoxy}acetic acid |
| 10 | Sodium {o-{6-[(2-chloro-α,α,6-tetrafluoro-p-tolyl)oxy]-1H-benzotriazol-1-yl}phenoxy}-acettate |
| 11 | Tert-butyl {o-{6-[(2-chloro-α,α,α,6-tetra-fluoro-p-tolyl)oxy]-1H-benzotriazol-1-yl}-phenoxy}acetate |

TABLE I

Preemergence Herbicidal Evaluations of Test Compounds

| Compound Number | Rate (kg/ha) | ABUTH | AMARE | AMBEL | CASOB | CHEAL | GALAP | IPOHE | DIGSA | ECHCG | SETVI | GLXMAW | ORYSA | ZEAMX |
|---|---|---|---|---|---|---|---|---|---|---|---|---|---|---|
| 1 | 0.500 | 9.0 | — | 9.0 | 5.0 | 9.0 | 7.0 | — | — | — | 7.0 | 3.0 | — | 2.0 |
|   | 0.250 | 9.0 | 9.0 | 8.0 | 8.0 | 9.0 | 7.0 | — | 4.0 | 2.0 | 4.0 | 4.5 | — | 4.0 |
|   | 0.125 | 9.0 | 9.0 | 8.7 | 3.0 | 9.0 | 7.0 | 0.0 | 5.5 | 1.5 | 4.3 | 5.3 | 0.0 | 2.0 |
| 2 | 0.500 | 9.0 | 9.0 | 9.0 | — | — | — | 9.0 | 9.0 | 5.0 | 9.0 | 9.0 | 4.0 | 2.0 |
|   | 0.250 | 9.0 | 9.0 | 8.7 | 9.0 | 9.0 | 9.0 | — | 9.0 | 6.0 | 8.3 | 6.3 | — | 3.0 |
|   | 0.125 | 9.0 | 9.0 | 8.3 | 9.0 | 9.0 | 9.0 | — | 9.0 | 3.0 | 9.0 | 2.0 | — | 2.0 |
| 3 | 0.500 | 9.0 | 9.0 | 9.0 | 8.0 | 9.0 | 8.0 | 9.0 | 9.0 | 5.0 | 9.0 | 1.5 | 0.0 | 0.5 |
|   | 0.250 | 7.5 | 9.0 | 8.5 | 8.0 | 9.0 | 8.0 | — | 8.5 | 4.0 | 8.5 | 6.0 | — | 1.5 |
|   | 0.125 | 0.0 | 9.0 | 6.5 | 9.0 | 9.0 | 6.0 | — | 7.5 | 3.0 | 0.0 | 2.0 | — | 1.0 |
| 4 | 0.500 | 9.0 | — | 0.0 | — | — | — | — | 0.0 | 0.0 | 7.0 | — | — | 0.0 |
| 5 | 0.500 | 9.0 | — | 9.0 | 9.0 | 9.0 | 9.0 | — | 0.0 | — | 7.0 | 7.0 | — | 0.0 |
|   | 0.250 | 9.0 | — | 6.0 | 8.0 | 9.0 | 9.0 | — | 7.0 | — | 7.0 | 7.0 | — | 0.0 |
|   | 0.125 | 0.0 | — | 8.0 | 8.0 | 9.0 | 9.0 | — | 0.0 | — | 8.0 | 2.0 | — | 0.0 |
| 6 | 0.500 | 9.0 | — | 0.0 | — | — | — | — | — | 0.0 | 0.0 | — | — | 0.0 |
| 7 | 0.500 | 9.0 | — | 8.0 | 9.0 | 9.0 | 9.0 | — | 0.0 | 2.0 | 6.0 | 1.0 | — | 0.0 |
|   | 0.250 | 9.0 | — | 7.0 | 9.0 | 9.0 | 8.0 | — | 5.0 | — | 5.0 | 0.0 | — | 0.0 |
|   | 0.125 | 6.0 | — | 6.0 | 7.0 | 9.0 | 6.0 | — | — | 0.0 | 2.0 | 0.0 | — | 0.0 |
| 8 | 0.500 | 6.0 | — | 7.5 | 7.0 | 9.0 | 4.0 | — | 2.0 | 0.0 | 5.0 | 0.0 | — | 0.0 |
|   | 0.250 | 0.0 | — | 4.0 | 4.0 | 9.0 | 0.0 | — | — | — | 5.0 | 0.0 | — | 0.0 |
|   | 0.125 | 0.0 | — | 3.0 | 9.0 | 9.0 | 0.0 | — | — | — | 0.0 | 0.0 | — | 0.0 |
| 9 | 0.500 | 9.0 | — | 7.0 | 6.0 | 9.0 | 8.0 | 9.0 | — | 7.0 | 9.0 | 9.0 | 4.0 | 5.0 |
| 10 | 0.500 | 9.0 | — | 7.0 | 7.0 | 9.0 | 9.0 | 9.0 | — | 6.0 | 9.0 | 5.0 | 6.0 | 5.0 |
| 11 | 0.500 | 5.0 | — | 0.0 | 0.0 | 9.0 | 5.0 | 4.0 | — | 0.0 | 0.0 | 4.0 | 0.0 | 0.0 |

EXAMPLE 18

Postemergence herbicidal evaluation of test compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 0.125 kg to 0.500 kg per hectare of test compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 17.

The data obtained are reported in Table II below. The compounds evaluated are reported by compound number given in Example 17.

TABLE II

Postemergence Herbicidal Evaluations of Test Compounds

| Compound Number | Rate (kg/ha) | ABUTH | AMARE | AMBEL | CASOB | CHEAL | GALAP | IPOHE | DIGSA | ECHCG | SETVI | GLXMAW | ORYSA | ZEAMX |
|---|---|---|---|---|---|---|---|---|---|---|---|---|---|---|
| 1 | 0.500 | 9.0 | — | 9.0 | — | — | — | — | 2.0 | 3.0 | 5.0 | — | — | 3.0 |
|   | 0.250 | 9.0 | — | 7.0 | 9.0 | 9.0 | — | — | 3.0 | 2.0 | 5.0 | 5.0 | — | 3.0 |
|   | 0.125 | 9.0 | — | 5.5 | 9.0 | 9.0 | — | — | 3.0 | 2.0 | 5.0 | 4.0 | — | 2.0 |
| 2 | 0.500 | 9.0 | 9.0 | 9.0 | — | — | — | 9.0 | 9.0 | 7.0 | 6.0 | 7.0 | 6.0 | 8.0 |
|   | 0.250 | 9.0 | 9.0 | 9.0 | — | — | — | 9.0 | 9.0 | 5.0 | 6.0 | 6.0 | 5.0 | 7.0 |
|   | 0.125 | 9.0 | 9.0 | 9.0 | — | — | — | 8.0 | 8.0 | 4.0 | 5.0 | 7.0 | 5.0 | 7.0 |
| 3 | 0.500 | 9.0 | 9.0 | 9.0 | — | — | — | 9.0 | 7.0 | 5.0 | 6.0 | 5.0 | 3.0 | 5.0 |
|   | 0.250 | 8.0 | 9.0 | 8.0 | — | — | — | 9.0 | 6.0 | 4.0 | 6.0 | 5.0 | 3.0 | 5.0 |
|   | 0.125 | 9.0 | 9.0 | 8.0 | 9.0 | 9.0 | — | 9.0 | 5.0 | 4.0 | 5.0 | 4.0 | 4.0 | 5.5 |
| 4 | 0.500 | 9.0 | 9.0 | 6.0 | — | — | — | 9.0 | 3.0 | 3.0 | 2.0 | 6.0 | 3.0 | 3.0 |
|   | 0.250 | 9.0 | 9.0 | 6.0 | — | — | — | 9.0 | 3.0 | 2.0 | 2.0 | 3.0 | 2.0 | 3.0 |
|   | 0.125 | 9.0 | 9.0 | 9.0 | — | — | — | 9.0 | 2.0 | 1.0 | 1.0 | 3.0 | 2.0 | 5.0 |
| 5 | 0.500 | 9.0 | 9.0 | 9.0 | — | — | — | 9.0 | 5.0 | 3.0 | 3.0 | 6.0 | 3.0 | 5.0 |
|   | 0.250 | 9.0 | 9.0 | 7.0 | 9.0 | 9.0 | — | 9.0 | 5.0 | 2.0 | 4.0 | 6.0 | 3.0 | 5.0 |
|   | 0.125 | 9.0 | 9.0 | 6.0 | — | — | — | 9.0 | 4.0 | 3.0 | 2.0 | 5.5 | 3.0 | 4.5 |
| 6 | 0.500 | 9.0 | 9.0 | 6.0 | — | — | — | 9.0 | 1.0 | 2.0 | 1.0 | 2.0 | 1.0 | 3.0 |
|   | 0.250 | 8.0 | 9.0 | 4.0 | 9.0 | — | — | 7.0 | 1.0 | 1.0 | 1.0 | 2.0 | 1.0 | 3.0 |
|   | 0.125 | 6.0 | 9.0 | 9.0 | — | — | — | 9.0 | 1.0 | 0.0 | 0.0 | 1.0 | 1.0 | 2.0 |
| 7 | 0.500 | 9.0 | 9.0 | 9.0 | — | — | — | 9.0 | 5.0 | 3.0 | 3.0 | 3.0 | 3.0 | 7.0 |
|   | 0.250 | 9.0 | 9.0 | 7.5 | 8.0 | 9.0 | — | 9.0 | 4.0 | 2.0 | 2.0 | 5.0 | 3.0 | 5.0 |
|   | 0.125 | 9.0 | 9.0 | 9.0 | — | — | — | 9.0 | 3.0 | 2.0 | 2.0 | 5.5 | 2.0 | 1.5 |
| 8 | 0.500 | 9.0 | 9.0 | 7.0 | 9.0 | 9.0 | — | 9.0 | 3.0 | 2.0 | 2.0 | 3.0 | 2.0 | 3.0 |
|   | 0.250 | 9.0 | 9.0 | 5.0 | 7.0 | 9.0 | 9.0 | 9.0 | 3.0 | 2.0 | 2.0 | 4.5 | 2.0 | 3.0 |
|   | 0.125 | 9.0 | 9.0 | 9.0 | 9.0 | 9.0 | 8.0 | 7.0 | 2.0 | 1.0 | 1.0 | 3.0 | 2.0 | 2.5 |
| 9 | 0.500 | 9.0 | — | 9.0 | 9.0 | 9.0 | 9.0 | 9.0 | — | 8.0 | 9.0 | 8.0 | 5.0 | 9.0 |
|   | 0.250 | 9.0 | — | 9.0 | 9.0 | 8.0 | 8.0 | 9.0 | — | 8.0 | 9.0 | 8.0 | 4.0 | 9.0 |
|   | 0.125 | 9.0 | — | 9.0 | 9.0 | 8.0 | 5.0 | 9.0 | — | 6.0 | 9.0 | 8.0 | 3.0 | 7.0 |
| 10 | 0.500 | 9.0 | — | 9.0 | 9.0 | 9.0 | 9.0 | 9.0 | — | 9.0 | 9.0 | 8.0 | 4.0 | 5.0 |
|    | 0.250 | 9.0 | — | 9.0 | 9.0 | 9.0 | 9.0 | 9.0 | — | 8.0 | 9.0 | 8.0 | 4.0 | 9.0 |
|    | 0.125 | 9.0 | — | 9.0 | 9.0 | 7.0 | 7.0 | 9.0 | — | 6.0 | 9.0 | 7.0 | 4.0 | 7.0 |
| 11 | 0.500 | 9.0 | — | 6.0 | 9.0 | 5.0 | 5.0 | 9.0 | — | 7.0 | 7.0 | 5.0 | 4.0 | 6.0 |
|    | 0.250 | 9.0 | — | 4.0 | 7.0 | 4.0 | 3.0 | 9.0 | — | 5.0 | 5.0 | 5.0 | 3.0 | 4.0 |
|    | 0.125 | 5.0 | — | 4.0 | 5.0 | 3.0 | 3.0 | 9.0 | — | 5.0 | 4.0 | 5.0 | 3.0 | 3.0 |

What is claimed is:
1. A compound having the structural formula

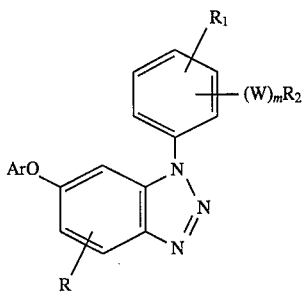

wherein
Ar is

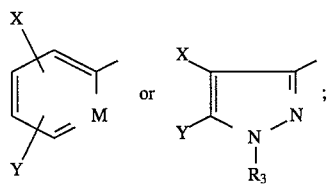

M is N or CZ

X, Y and Z are each independently hydrogen, halogen, $C_1-C_4$alkyl, $C_1-C_4$haloalkyl, $C_1-C_4$alkoxy, $C_1-C_4$haloalkoxy, cyano, nitro or $S(O)_pR_4$ with the proviso that X, Y and Z cannot simultaneously be nitro;

R is hydrogen, halogen, nitro, cyano, $C_1-C_4$alkyl, $C_1-C_4$haloalkyl, $C_1-C_4$alkoxy, $C_1-C_4$haloalkoxy or $S(O)_qR_5$;

p and q are each independently an integer of 0, 1 or 2;

$R_4$ and $R_5$ are each independently $C_1-C_4$alkyl optionally substituted with one or more halogen atoms;

$R_3$ is $C_1-C_4$alkyl;

$R_1$ is hydrogen, halogen, $C_1-C_4$alkyl or $C_1-C_4$haloalkyl;

W is O, S or $NR_6$;

$R_6$ is hydrogen or $C_1-C_4$alkyl;

m is an integer of 0 or 1;

$R_2$ is V or $R_7V$;

$R_7$ is $C_1-C_5$alkylene optionally substituted with one or more halogen, $C_1-C_4$alkyl, $C_1-C_4$haloalkyl or $C_3-C_6$cycloalkyl groups;

V is cyano, $C(O)R_8$, $C(Q)R_9$, $CH_2OC(O)R_{10}$, $CH_2OR_9$, $CH(OR_{11})_2$, $N(R_9)SO_2R_{12}$ or $C_2-C_6$alkenyl substituted with one $CO_2R_{10}$ group;

$R_8$ is OH, $OR_{13}$, $NR_{14}R_{15}$ or $N(R_9)SO_2R_{12}$;

Q is O, $NOC(R_{16}R_{17})CO_2R_{11}$ or $NOR_{10}$;

$R_9$ is hydrogen or $C_1-C_4$alkyl optionally substituted with $C_1-C_4$alkoxy;

$R_{10}$ is hydrogen, $C_1-C_4$alkyl, benzyl or phenyl optionally substituted with one or more halogen, cyano, nitro, $C_1-C_4$alkyl, $C_1-C_4$haloalkyl, $C_1-C_4$alkoxy or $C_1-C_4$haloalkoxy groups;

$R_{11}$ is $C_1-C_4$alkyl, $-(CH_2)_3-$ or $-(CH_2)_4-$;

$R_{12}$ is $C_1-C_4$alkyl, $C_1-C_4$haloalkyl or phenyl optionally substituted with one or more halogen, cyano, nitro, $C_1-C_4$alkyl, $C_1-C_4$haloalkyl, $C_1-C_4$alkoxy or $C_1-C_4$haloalkoxy groups;

$R_{13}$ is
$C_1-C_6$alkyl optionally substituted with $C_1-C_4$ alkoxy, $C_1-C_4$alkylthio, halogen, hydroxy, $C_3-C_6$cycloalkyl, furyl or phenyl optionally substituted with one or more halogen, cyano, nitro, $C_1-C_4$alkyl, $C_1-C_4$haloalkyl, $C_1-C_4$alkoxy or $C_1-C_4$haloalkoxy groups, $C_3-C_6$alkenyl optionally substituted with $C_1-C_4$alkoxy, halogen, $C_3-C_6$cycloalkyl or phenyl optionally substituted with one or more halogen, cyano, nitro, $C_1-C_4$alkyl, $C_1-C_4$haloalkyl, $C_1-C_4$alkoxy or $C_1-C_4$haloalkoxy groups, $C_3-C_6$alkynyl optionally substituted with $C_1-C_4$alkoxy or halogen, $C_3-C_6$cycloalkyl, $N=C(R_{16}R_{17})$, $C(R_{16}R_{17})CO_2R_9$ or an alkali metal, alkaline earth metal, manganese, copper, zinc, cobalt, silver, nickel, ammonium or organic ammonium cation;

$R_{14}$ and $R_{15}$ are each independently hydrogen, $C_1-C_4$alkyl or phenyl optionally substituted with one or more halogen, cyano, nitro, $C_1-C_4$alkyl, $C_1-C_4$haloalkyl, $C_1-C_4$alkoxy or $C_1-C_4$haloalkoxy groups; and $R_{16}$ and $R_{17}$ are each independently hydrogen or $C_1-C_4$alkyl.

2. The compound according to claim 1 wherein
X, Y and Z are each independently hydrogen, halogen or $C_1-C_4$haloalkyl;
R is hydrogen or halogen;
$R_1$ is hydrogen;
W is O;
$R_7$ is $C_1-C_5$alkylene optionally substituted with one or more $C_1-C_4$alkyl groups;
V is $C(O)R_8$;
$R_8$ is OH or $OR_{13}$; and
$R_{13}$ is $C_1-C_6$alkyl, $C_3-C_6$alkenyl, $C_3-C_6$alkynyl or an alkali metal, alkaline earth metal, ammonium or tri($C_1-C_6$alkyl)ammonium cation.

3. The compound according to claim 2 having the structural formula

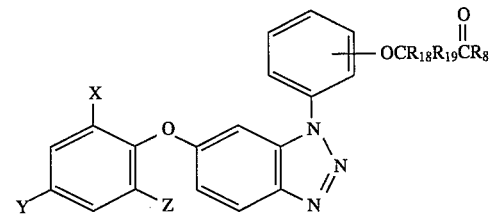

wherein
X is hydrogen, halogen or $CF_3$;
Y and Z are each independently halogen or $CF_3$;
$R_{13}$ is $C_1-C_4$alkyl or an alkali metal, alkaline earth metal, ammonium or tri($C_1-C_6$alkyl)ammonium cation; and
$R_{18}$ and $R_{19}$ are each independently hydrogen or $C_1-C_4$alkyl.

4. The compound according to claim 3 methyl 2-{o-{6-[(2-chloro-α,α,α,6-tetrafluoro-p-tolyl)oxy]-1H-benzotriazol-1-yl}phenoxy}propionate.

5. The compound according to claim 3 {o-{6-[(2-chloro-α,α,α,6-tetrafluoro-p-tolyl)oxy]-1H-benzotriazol-1-yl}phenoxy}acetic acid.

6. The compound according to claim 3 {o-{[6-(2-chloro-α,α,α-trifluoro-p-tolyl)oxy]-1H-benzotriazol-1-yl}phenoxy}acetic acid.

7. The compound according to claim 3 sodium {o-{6-[(2-chloro-α,α,α,6-tetrafluoro-p-tolyl)oxy]- 1H-benzotriazol-1-yl}phenoxy}acetate.

8. The compound according to claim 3 methyl {o-{6-[(2-chloro-α,α,α-trifluoro-p-tolyl)oxy]-1H-benzotriazol-1-yl}phenoxy}acetate.

9. The compound according to claim 3 {o-[6-(2,4-dichlorophenoxy)-1H-benzotriazol-1-yl] phenoxy}acetic acid.

10. The compound according to claim 3 methyl {o-{6-[(2-chloro-α,α,α,6-tetrafluoro-p-tolyl)oxy]- 1H-benzotriazol-1-yl}phenoxy}acetate.

11. The compound according to claim 3 methyl 2-{p-{6-[(2-chloro-α,α,α,6-tetrafluoro-p-tolyl)oxy]- 1H-benzotriazol-1-yl}phenoxy}propionate.

12. A method for controlling undesirable plant species which comprises applying to the foliage of said plants or to the soil or water containing seeds or other propagating organs thereof, a herbicidally effective amount of a compound having the structural formula

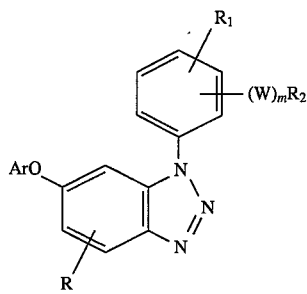

wherein Ar, W, m, R, $R_1$ and $R_2$ are described in claim 1.

13. The method according to claim 12 wherein

X, Y and Z are each independently hydrogen, halogen or $C_1$–$C_4$haloalkyl;

R is hydrogen or halogen;

$R_1$ is hydrogen;

W is O;

$R_7$ is $C_1$–$C_5$alkylene optionally substituted with one or more $C_1$–$C_4$alkyl groups;

V is $C(O)R_8$;

$R_8$ is OH or $OR_{13}$; and $R_{13}$ is $C_1$–$C_6$alkyl, $C_3$–$C_6$alkenyl, $C_3$–$C_6$alkynyl or an alkali metal, alkaline earth metal, ammonium or tri($C_2$–$C_6$alkyl)ammonium cation.

14. The method according to claim 13 wherein the compound has the structural formula

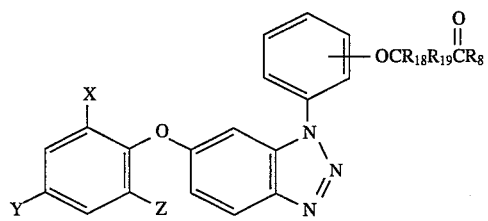

wherein

X is hydrogen, halogen or $CF_3$;

Y and Z are each independently halogen or $CF_3$;

$R_{13}$ is $C_1$–$C_4$alkyl or an alkali metal, alkaline earth metal, ammonium or tri($C_1$–$C_6$alkyl)ammonium cation; and $R_{18}$ and $R_{19}$ are each independently hydrogen or $C_1$–$C_4$alkyl.

15. The method according to claim 14 wherein the compound is selected from the group consisting of methyl 2-{o-{6-[(2-chloro-α,α,α,6-tetrafluoro-p-tolyl)oxy]-1H-benzotriazol-1-yl}phenoxy}propionate;

{o-{6-[(2-chloro-α,α,α,6-tetrafluoro-p-tolyl)oxy]-1H-benzotriazol-1-yl}phenoxy}acetic acid;

{o-{[6-(2-chloro-α,α,α-trifluoro-p-tolyl)oxy]-1H-benzotriazol-1-yl}phenoxy}acetic acid;

sodium {o-{6-[(2-chloro-α,α,α,6-tetrafluoro-p-tolyl)oxy] 1H-benzotriazol-1-yl}phenoxy}acetate;

methyl {o-{6-[(2-chloro-α,α,α-trifluoro-p-tolyl) oxy]-1H-benzotriazol-1-yl}phenoxy}acetate;

{o-[6-(2,4-dichlorophenoxy)-1H-benzotriazol-1yl] phenoxy}acetic acid;

methyl {o-{6-[(2-chloro-α,α,α,6-tetrafluoro-p-tolyl)oxy]-1H-benzotriazol-1-yl}phenoxy}acetate; and methyl 2-{p-{6-[(2-chloro-α,α,α,6-tetrafluoro-p-tolyl)oxy] -1H-benzotriazol-1-yl}phenoxy}propionate.

16. The method according to claim 12 which comprises applying said compound to the foliage of said plants at a rate of about 0.016 kg/ha to 4 kg/ha.

17. A herbicidal composition which comprises and inert solid or liquid carrier and a herbicidally effective amount of a compound having the structural formula

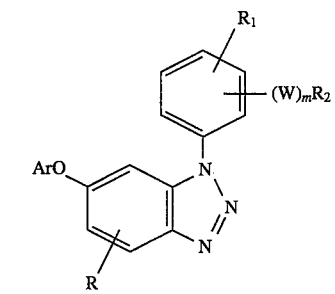

wherein Ar, W, m, R, $R_1$ and $R_2$ are described in claim 1.

18. The composition according to claim 17 wherein

X, Y and Z are each independently hydrogen, halogen or $C_1$–$C_4$haloalkyl;

R is hydrogen or halogen;

$R_1$ is hydrogen;

W is O;

$R_7$ is $C_1$–$C_5$alkylene optionally substituted with one or more $C_1$–$C_4$alkyl groups;

V is $C(O)R_8$;

$R_8$ is OH or $OR_{13}$; and $R_{13}$ is $C_1$–$C_6$alkyl, $C_3$–$C_6$alkenyl, $C_3$–$C_6$alkynyl or an alkali metal, alkaline earth metal, ammonium or tri($C_1$–$C_6$alkyl)ammonium cation.

19. The composition according to claim 18 wherein the compound has the structural formula

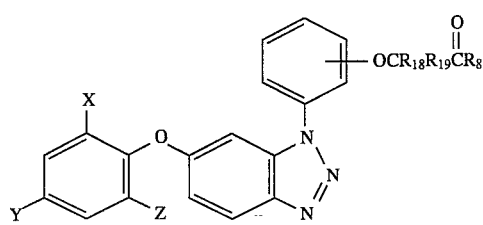
wherein
X is hydrogen, halogen or $CF_3$;
Y and Z are each independently halogen or $CF_3$;
$R_{13}$ is $C_1$–$C_4$alkyl or an alkali metal, alkaline earth metal, ammonium or tri($C_1$–$C_6$alkyl)ammonium cation; and
$R_{18}$ and $R_{19}$ are each independently hydrogen or $C_1$–$C_4$alkyl.
* * * * *